United States Patent [19]

Wood et al.

[11] Patent Number: 4,869,901
[45] Date of Patent: Sep. 26, 1989

[54] METHOD AND COMPOSITIONS FOR HELMINTIC, ARTHROPOD ECTOPARASITIC AND ACARIDAL INFECTIONS WITH NOVEL AGENTS

[75] Inventors: Irwin B. Wood, Willow Grove, Pa.; John A. Pankavich, Trenton, N.J.

[73] Assignee: American Cyanamid Company, Stamford, Conn.

[21] Appl. No.: 617,649

[22] Filed: Jun. 5, 1984

[51] Int. Cl.$^4$ .................... A61K 35/74; A61K 37/00; C12P 1/06
[52] U.S. Cl. .................................. 424/115; 424/43; 424/122; 435/169
[58] Field of Search .................... 424/122, 93, 115; 435/169

*Primary Examiner*—Jerome D. Goldberg
*Attorney, Agent, or Firm*—Estelle J. Tsevdos

[57] ABSTRACT

The present invention relates to methods and compositions for the control and prevention of helmintic, arthropod ectoparasitic and acaridal infections, in warm-blooded animals, such as meat-producing animals, and poultry, by administering to said animals a therapeutically or prophylactically-effective amount of new agents designated LL-F28249$\alpha$, $\beta$, $\gamma$, $\delta$, $\epsilon$, $\zeta$, $\eta$, $\theta$, $\iota$ and $\omega$, or mixtures thereof. The invention also relates to methods for the control of plant nematode infestations. These novel agents are produced via a controlled conditioned microbiological fermentation using Streptomyces sp. LL-F28249, having deposit accession number NRRL 15773.

4 Claims, 37 Drawing Sheets

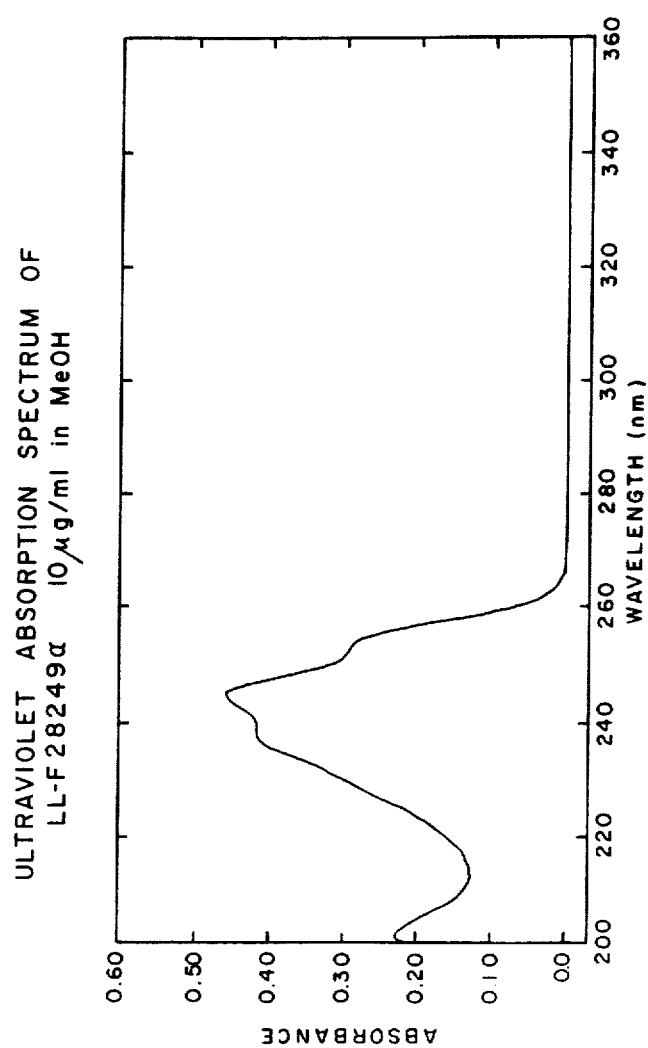
FIGURE I

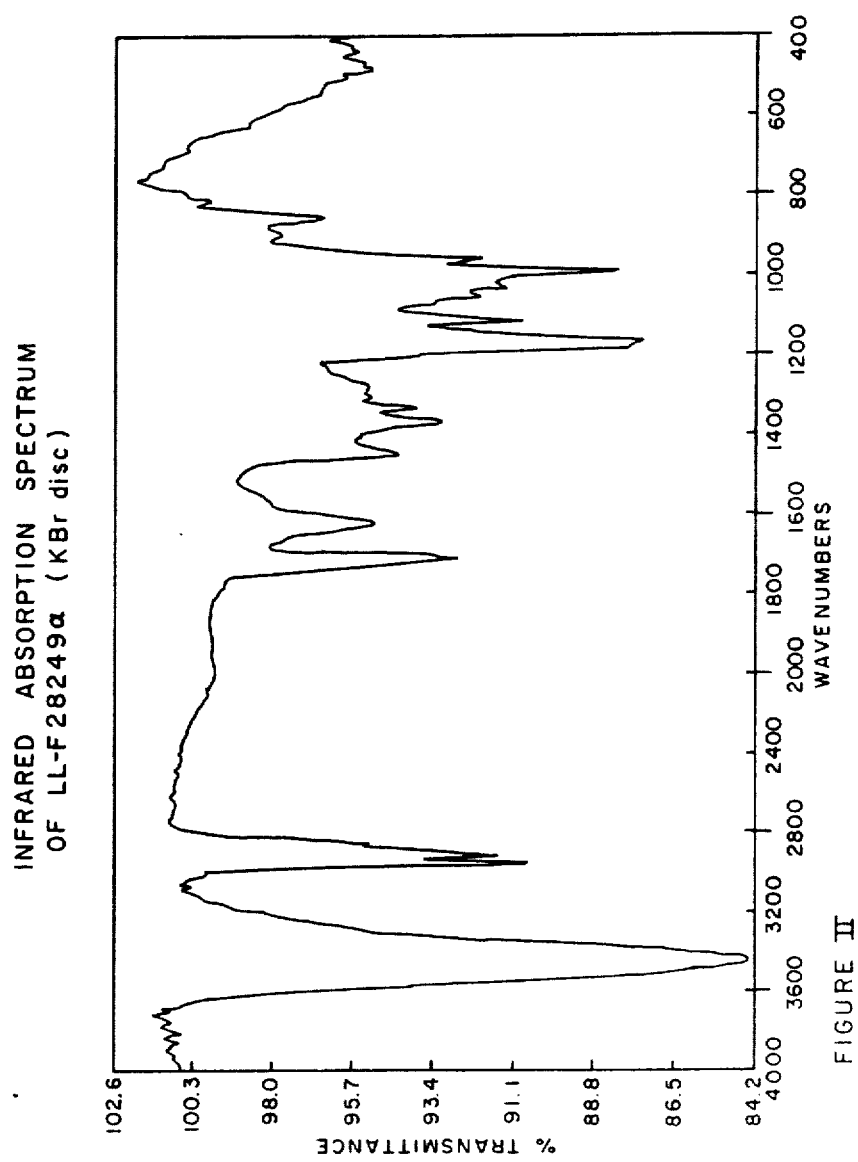

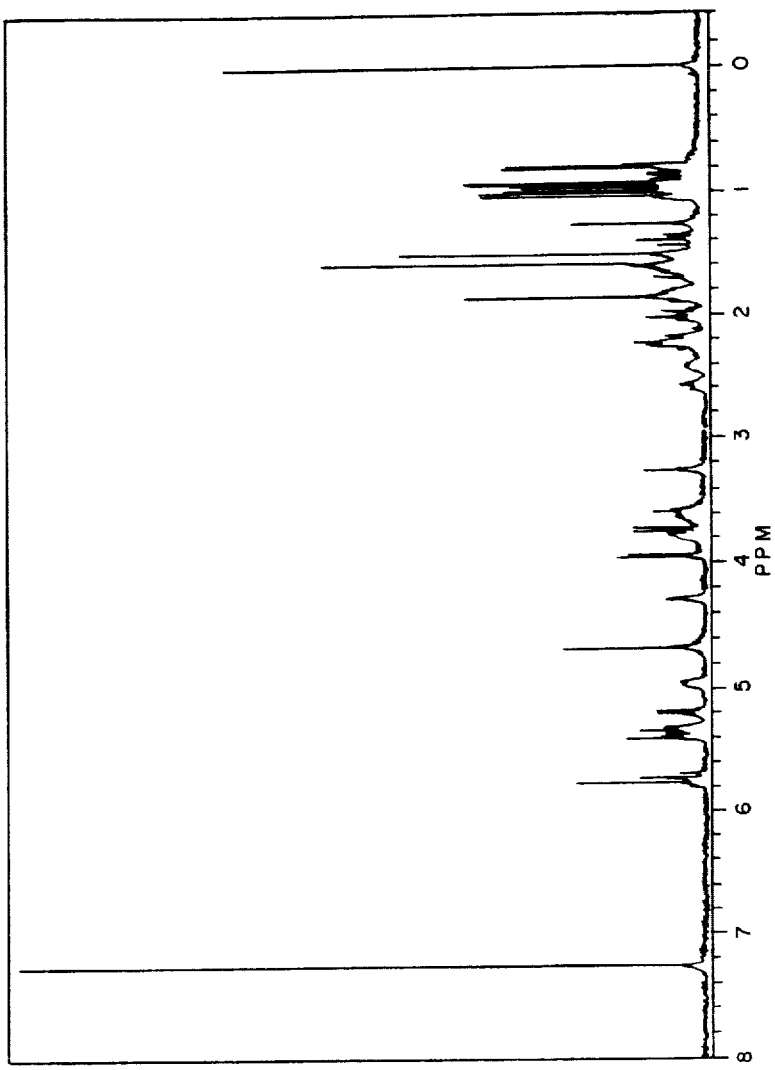

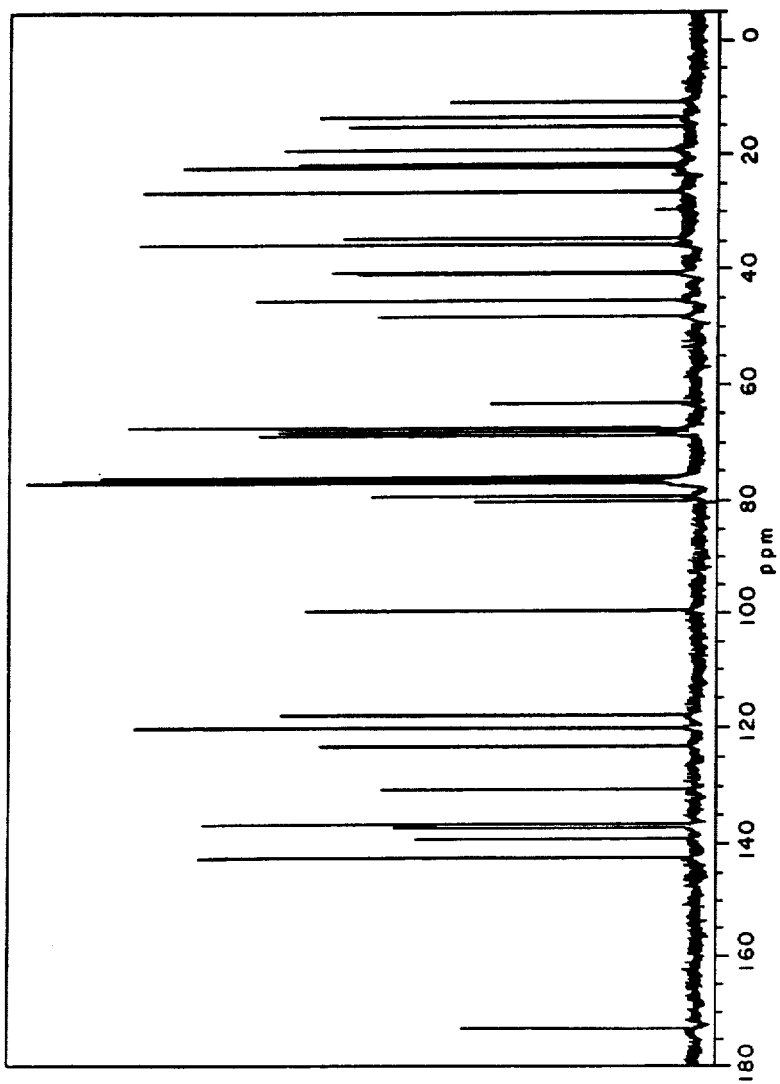
FIGURE IV

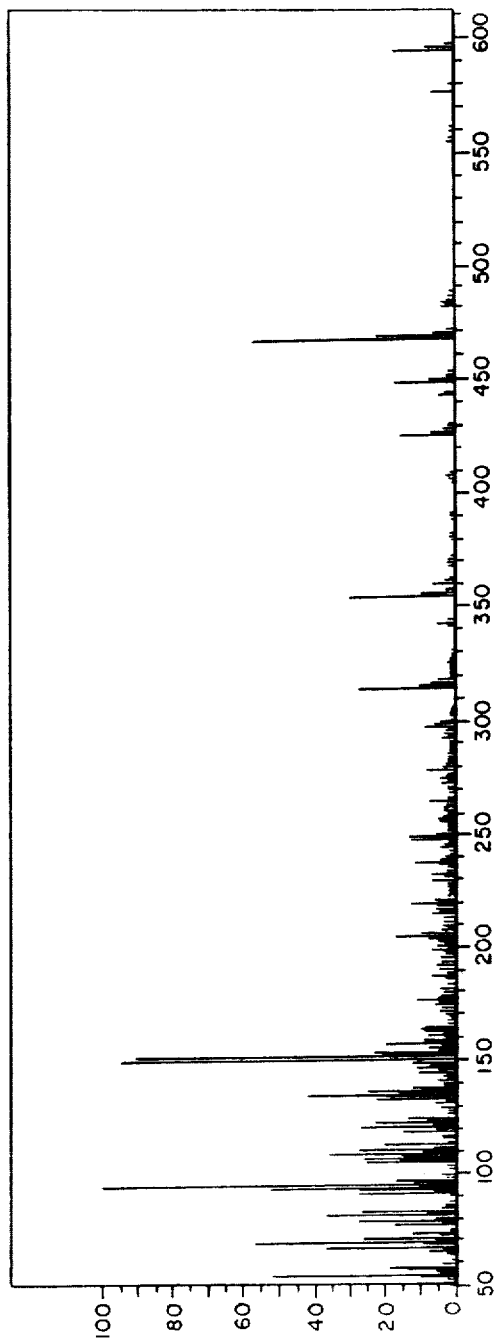

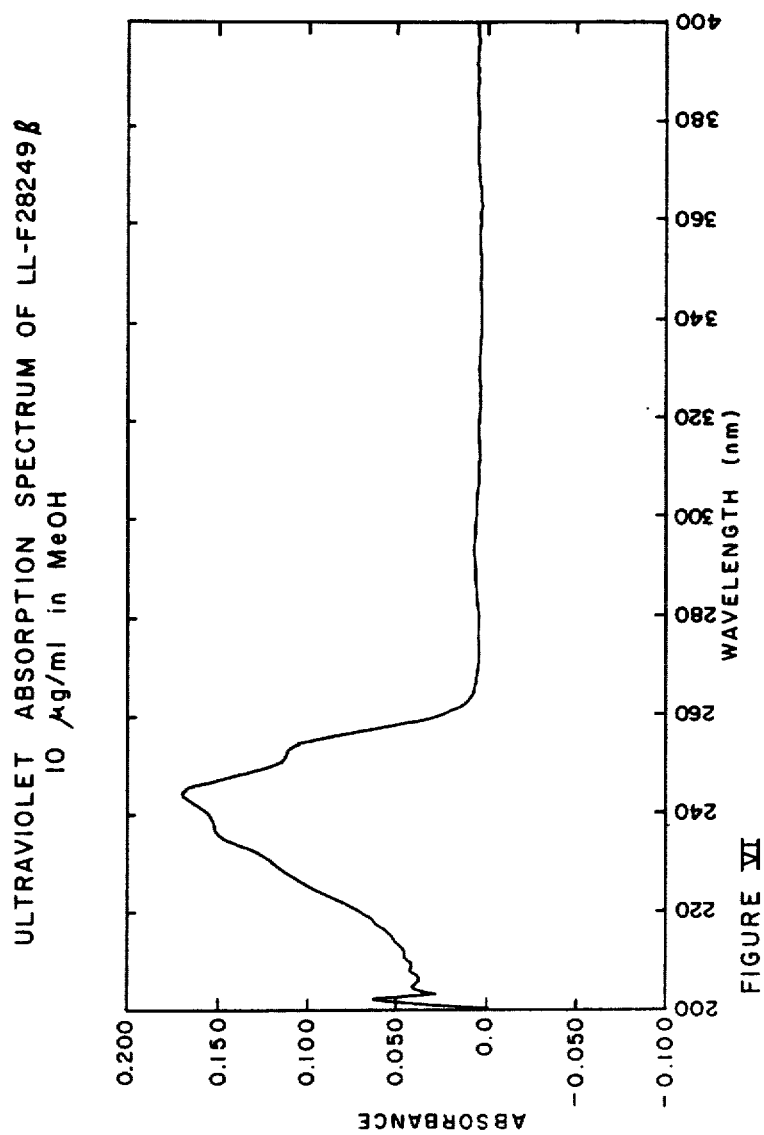
FIGURE VI

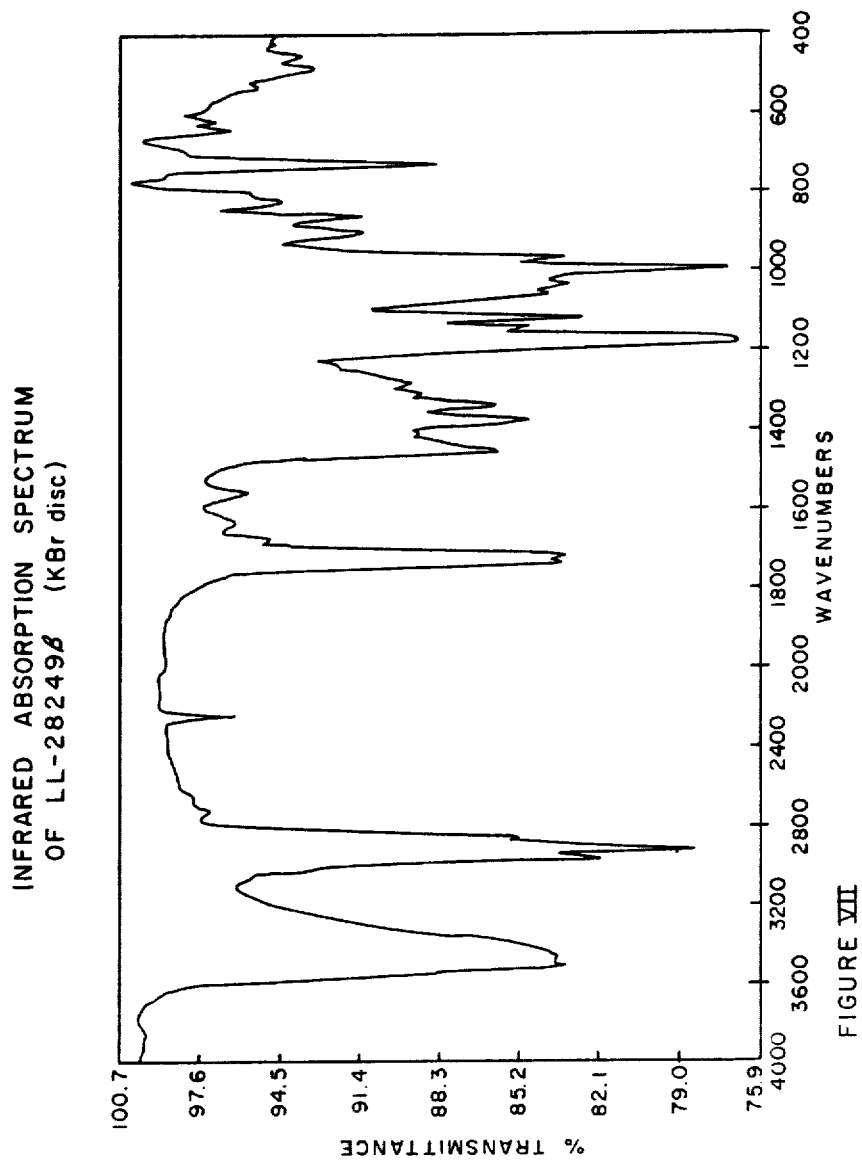

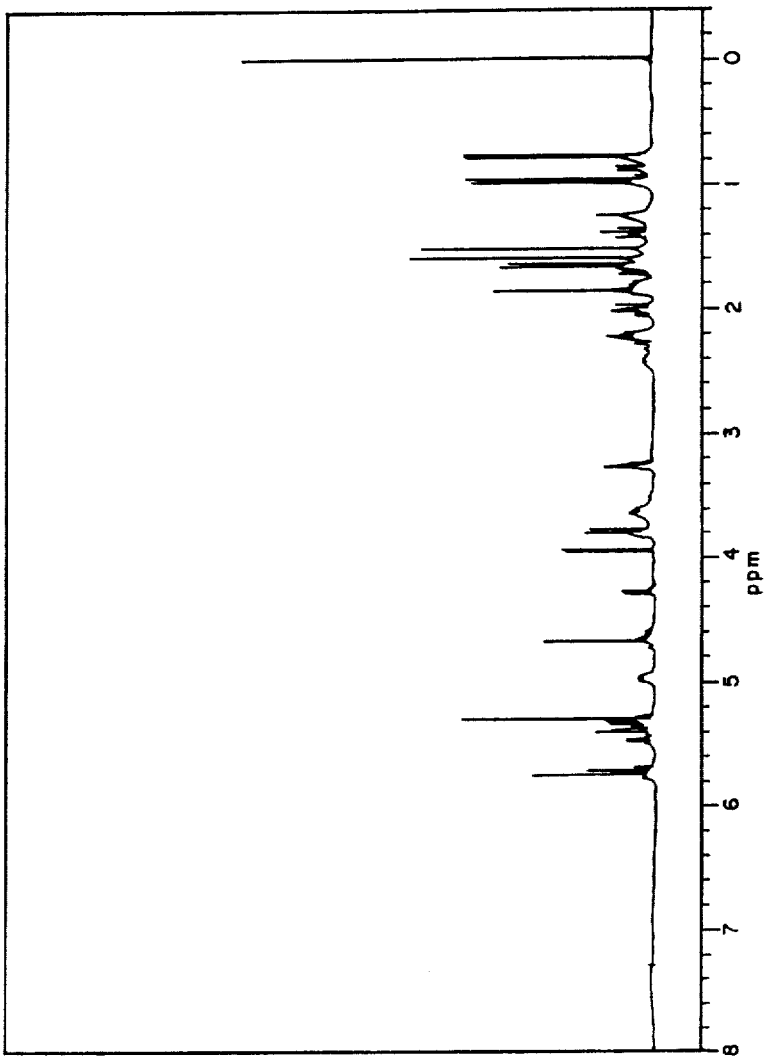
FIGURE VIII

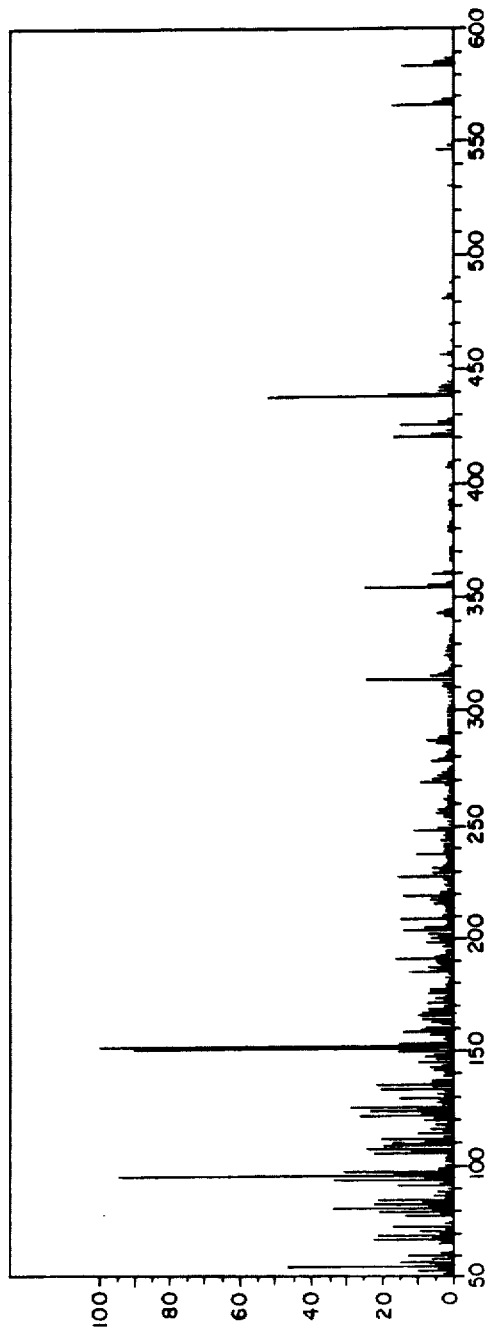
FIGURE IX

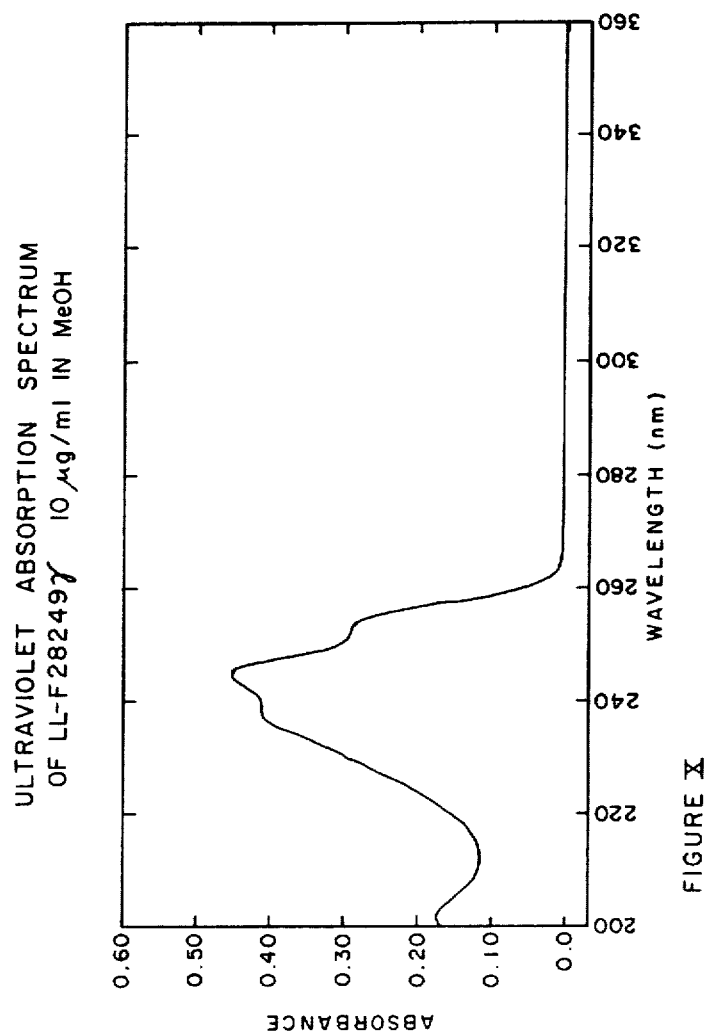

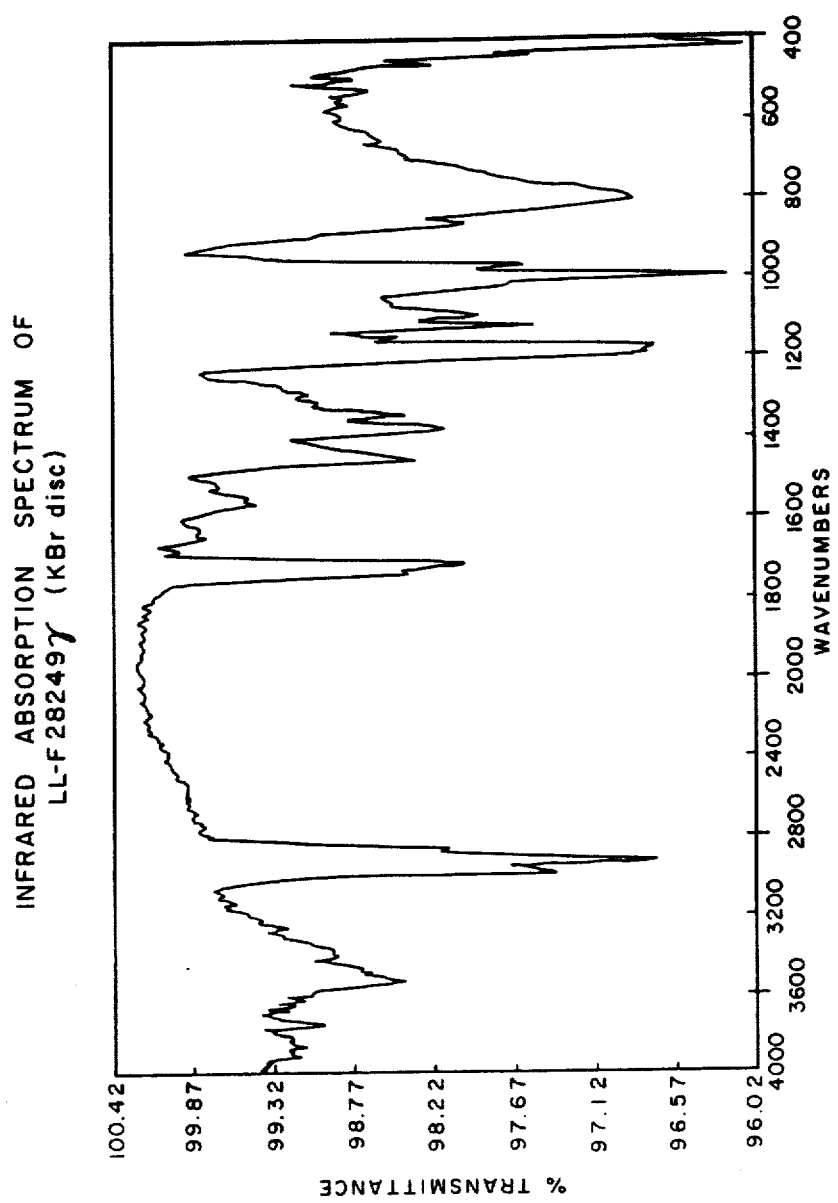
FIGURE XI

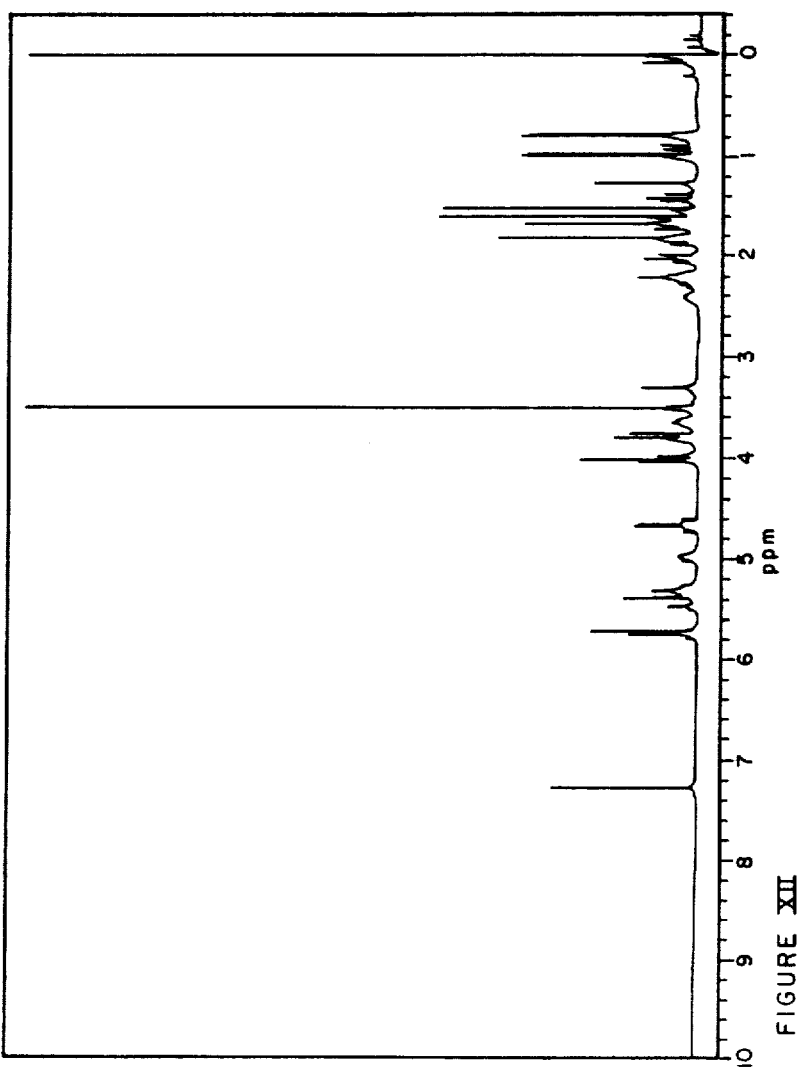
FIGURE XII

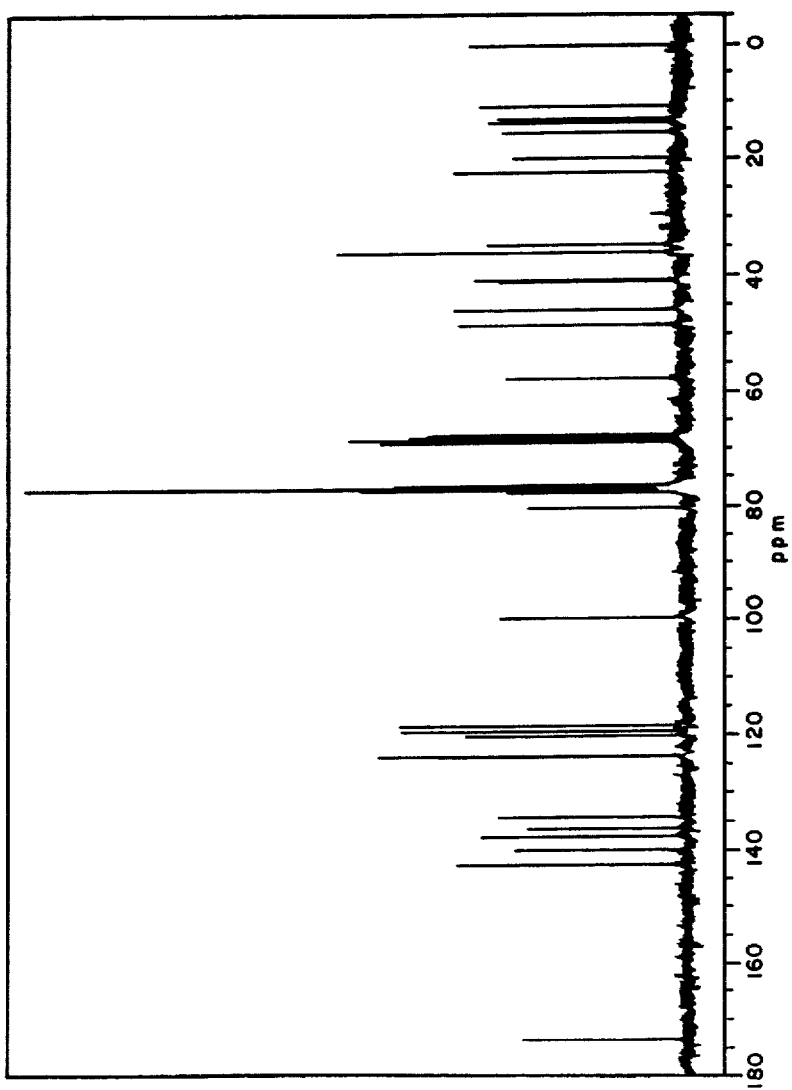
FIGURE XIII

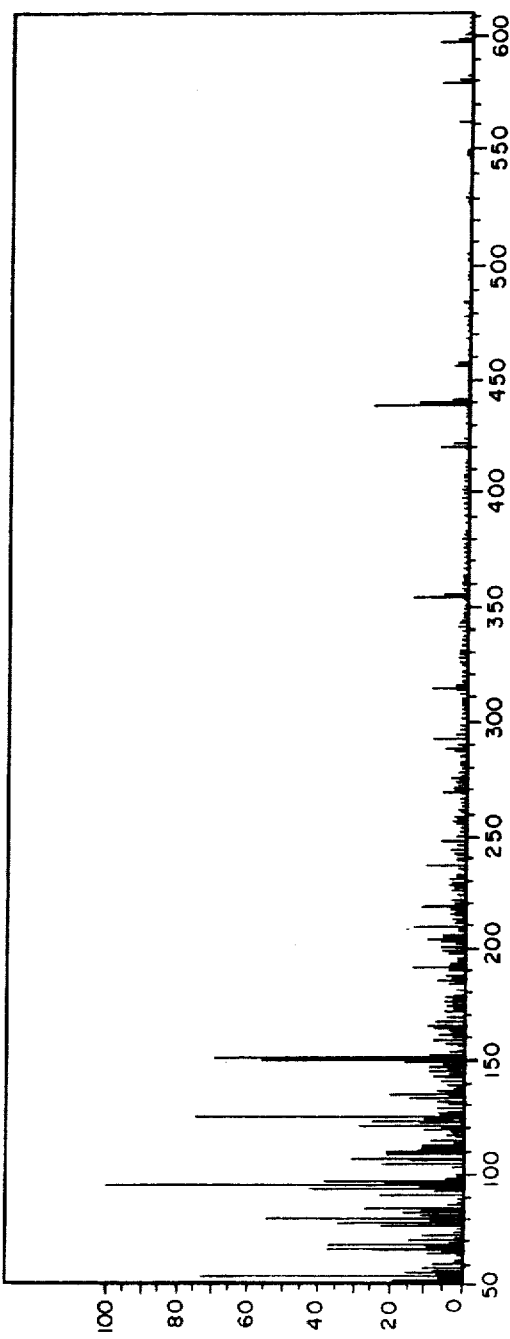
FIGURE XIV

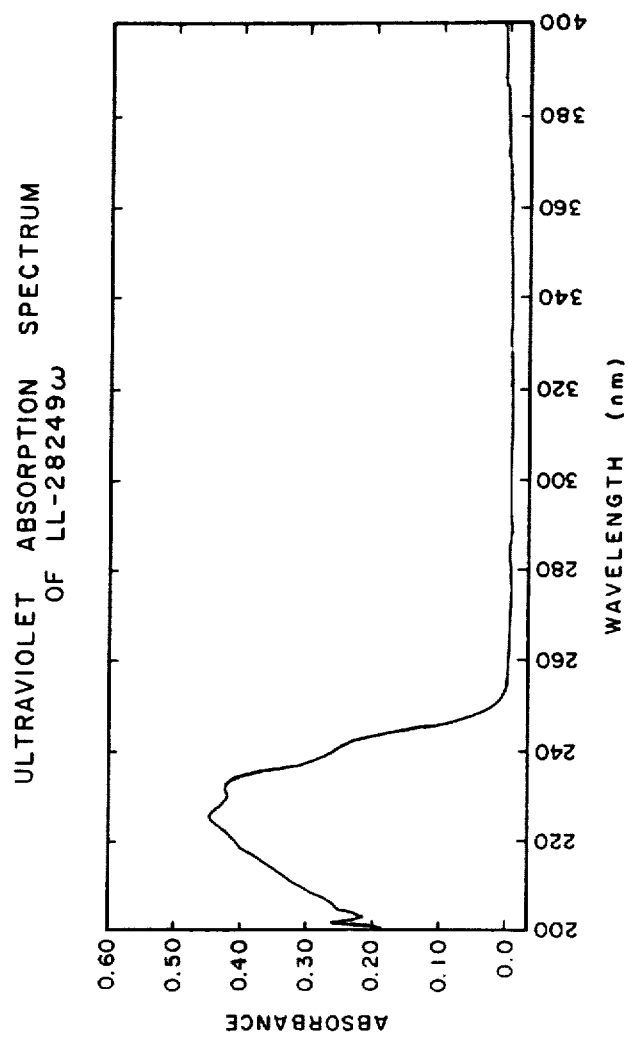
FIGURE XV

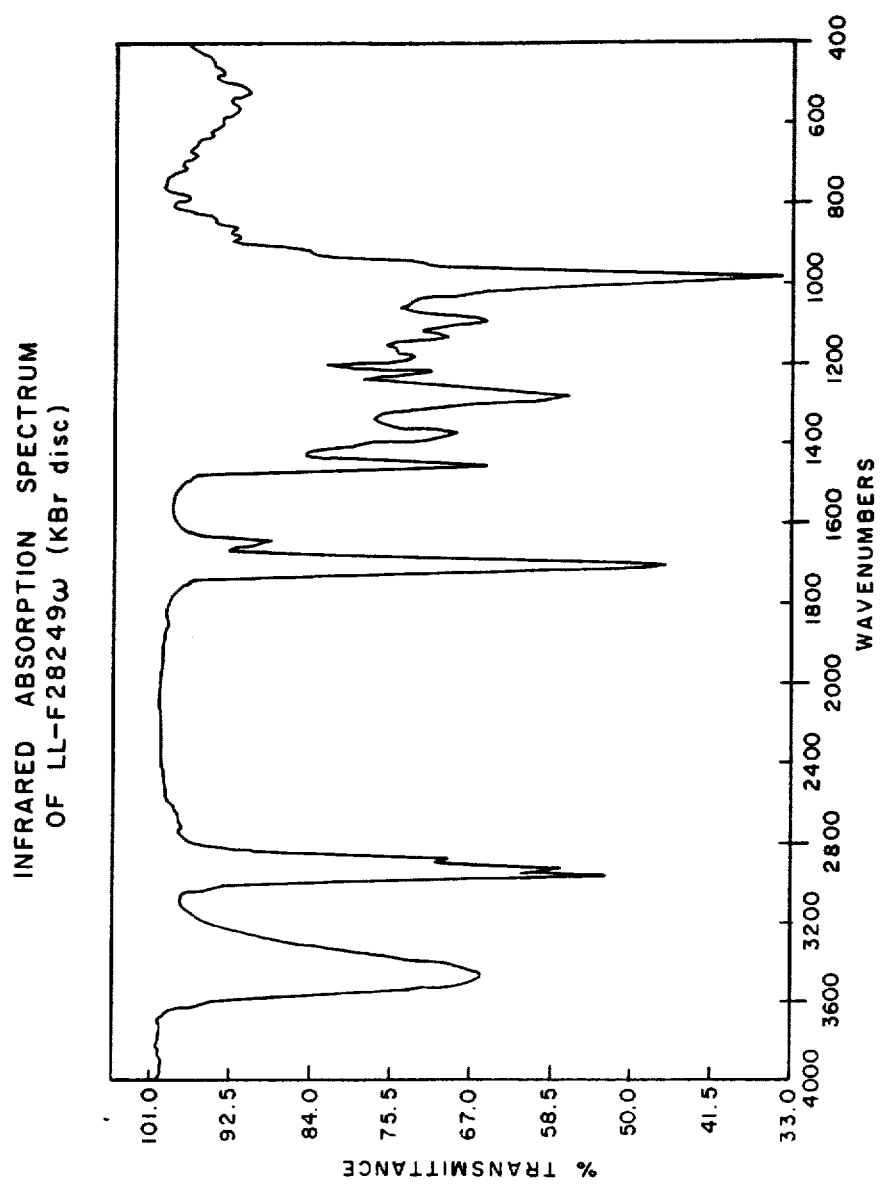
FIGURE XVI

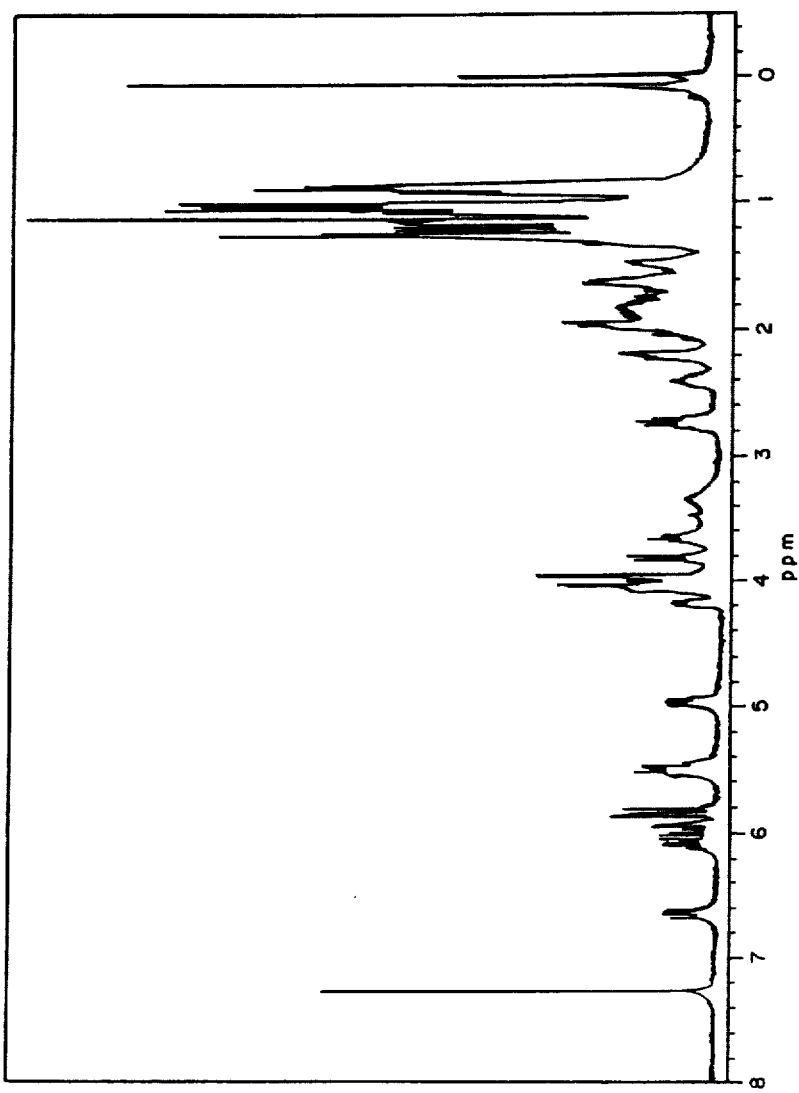
FIGURE XVII

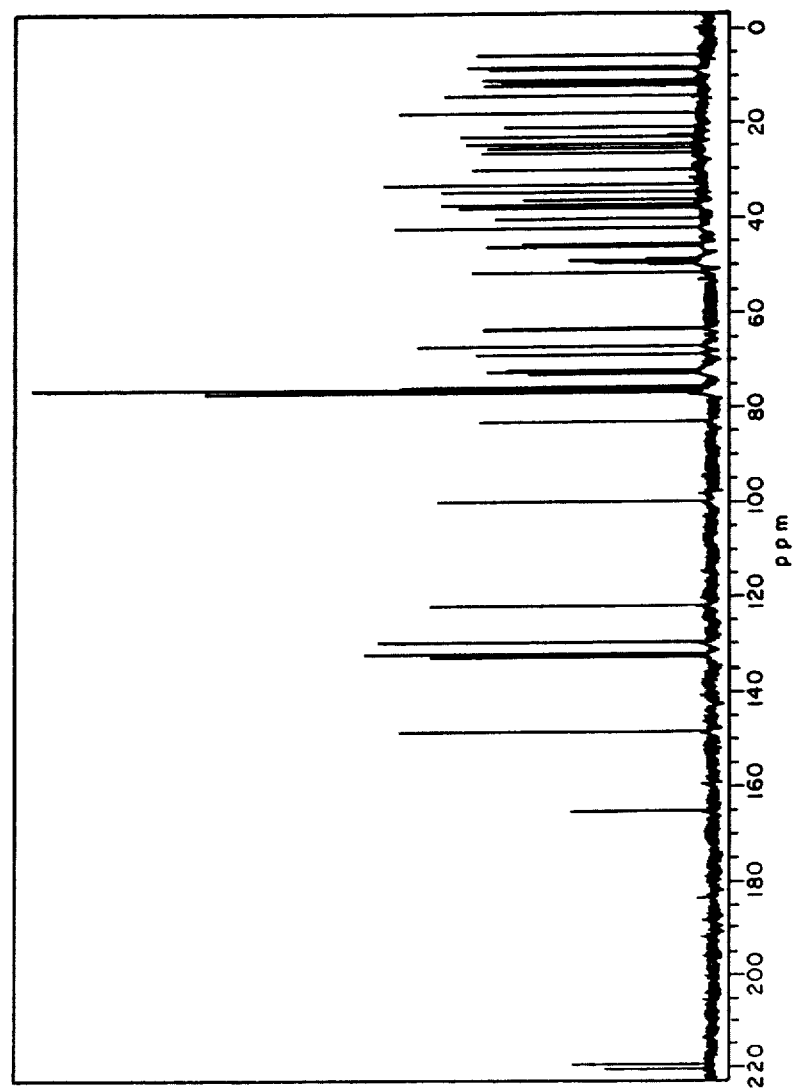
FIGURE XVIII

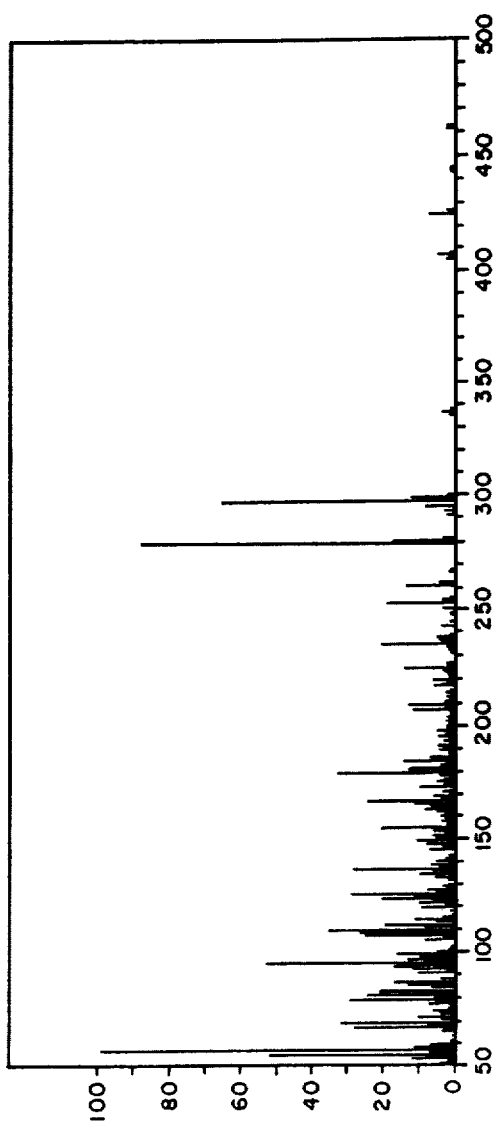
FIGURE XIX

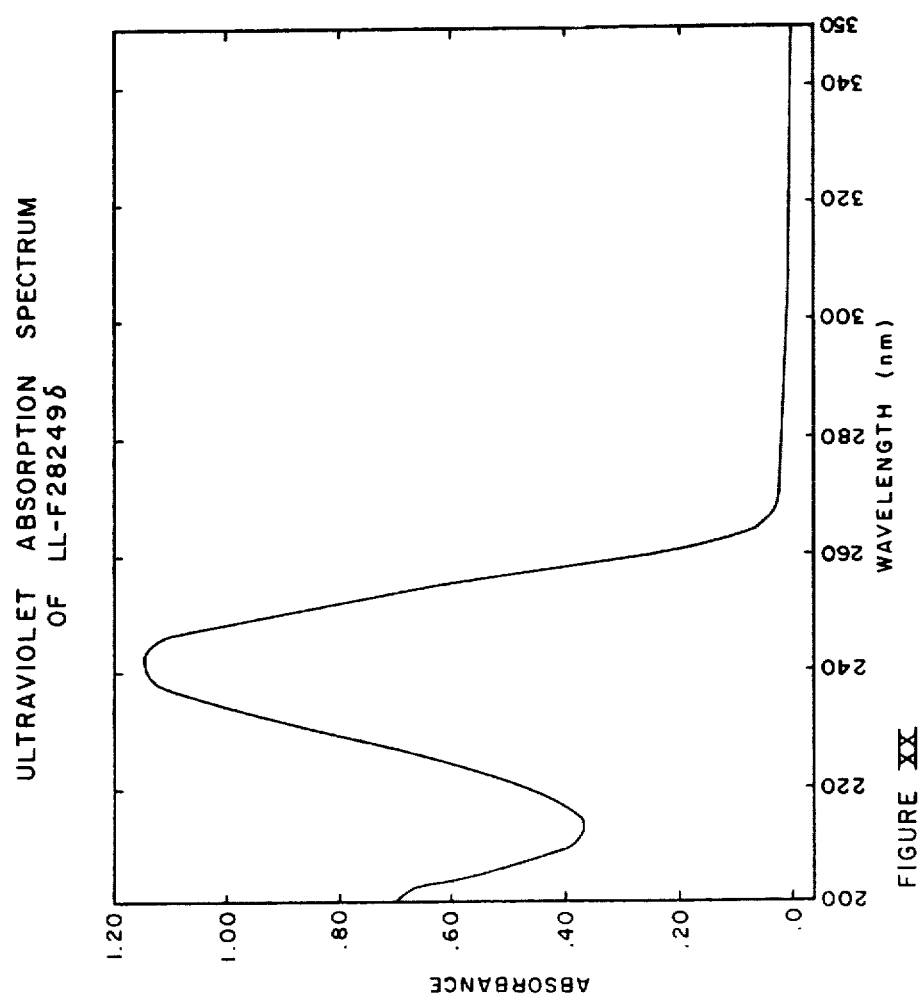
FIGURE XX

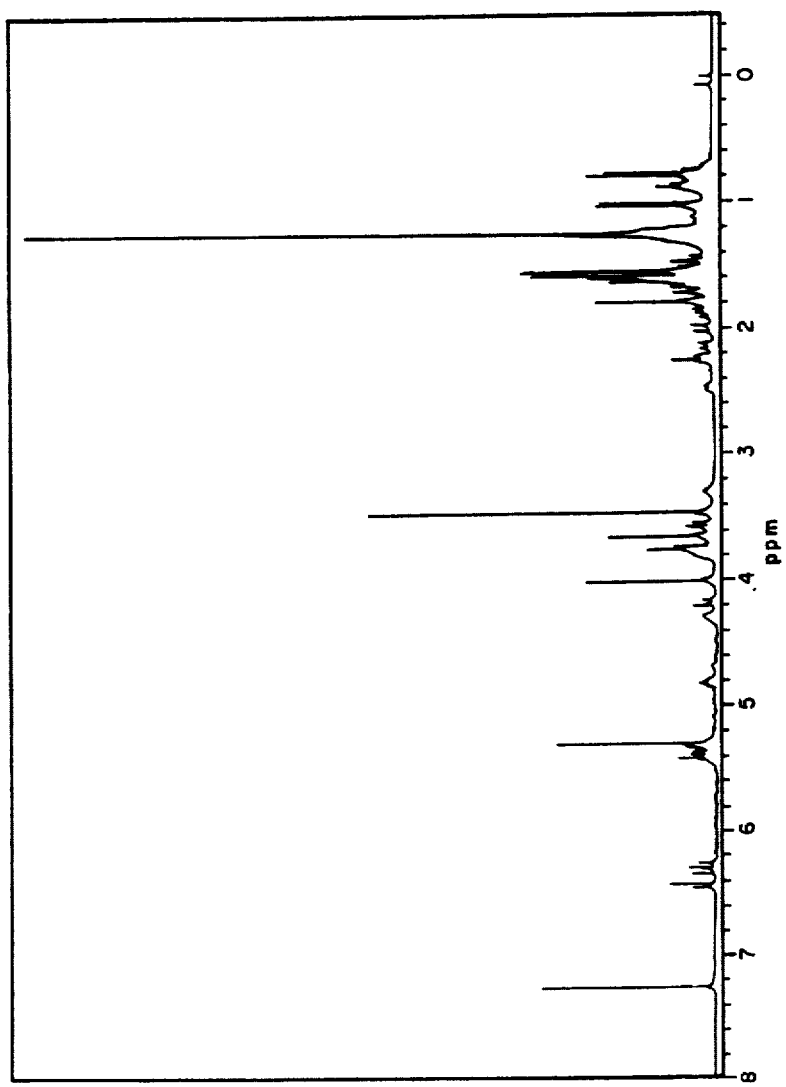

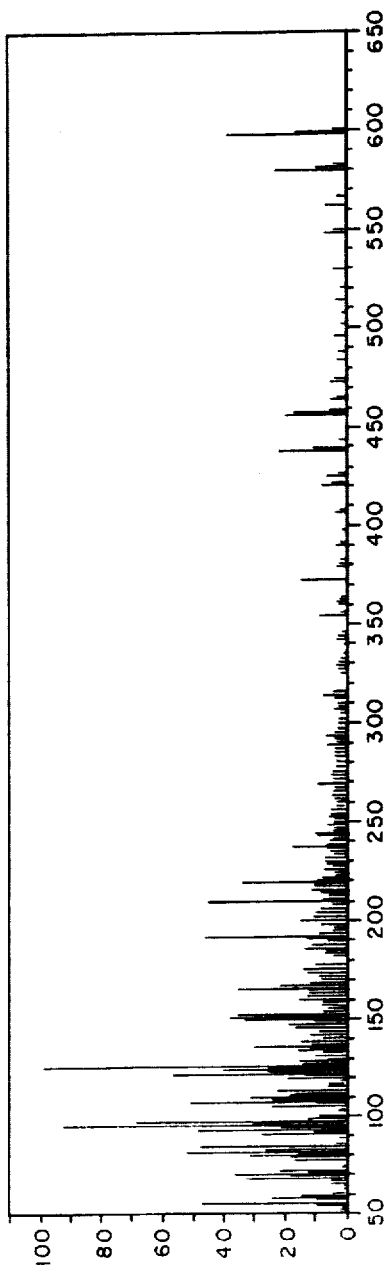
FIGURE XXII

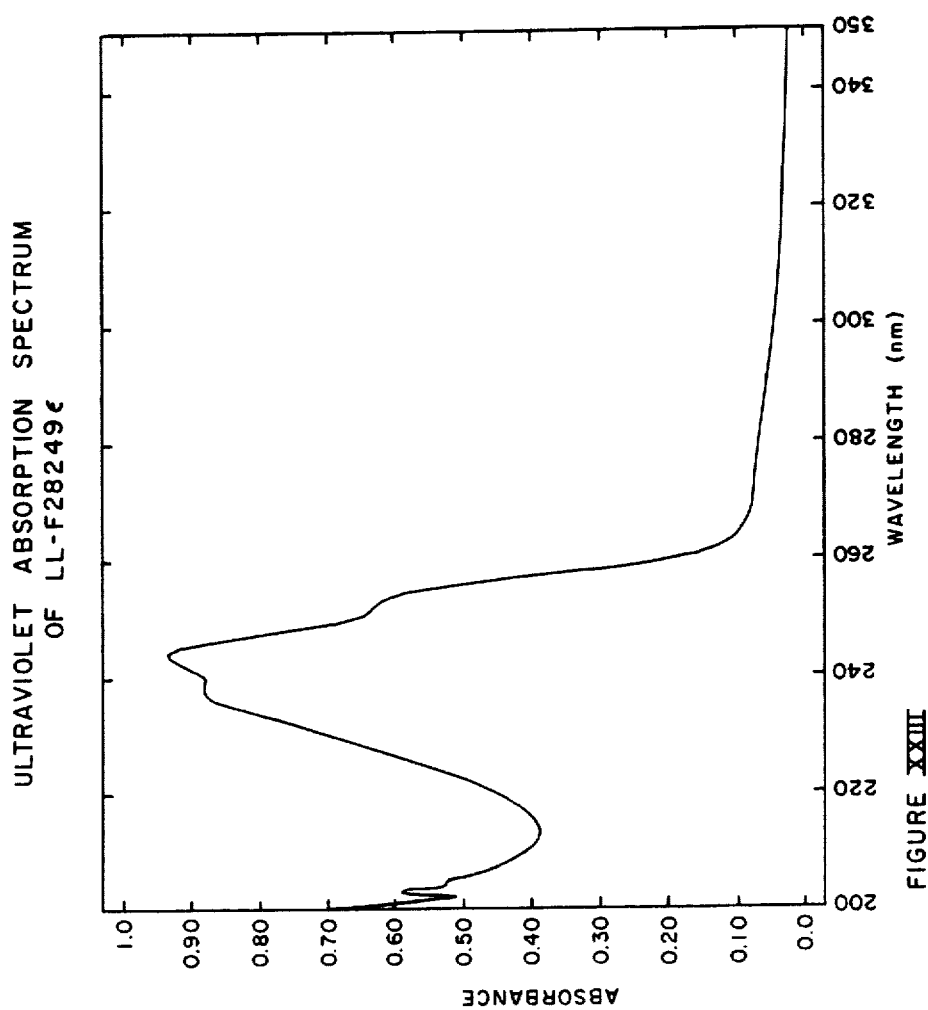

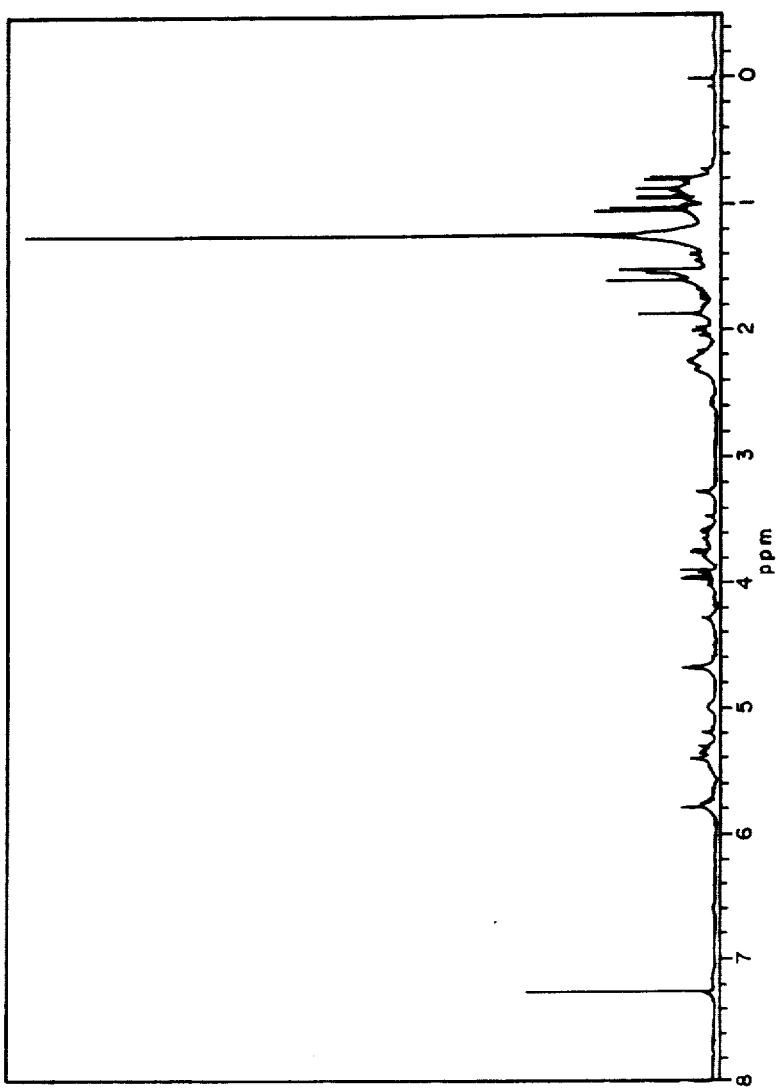
FIGURE XXIV

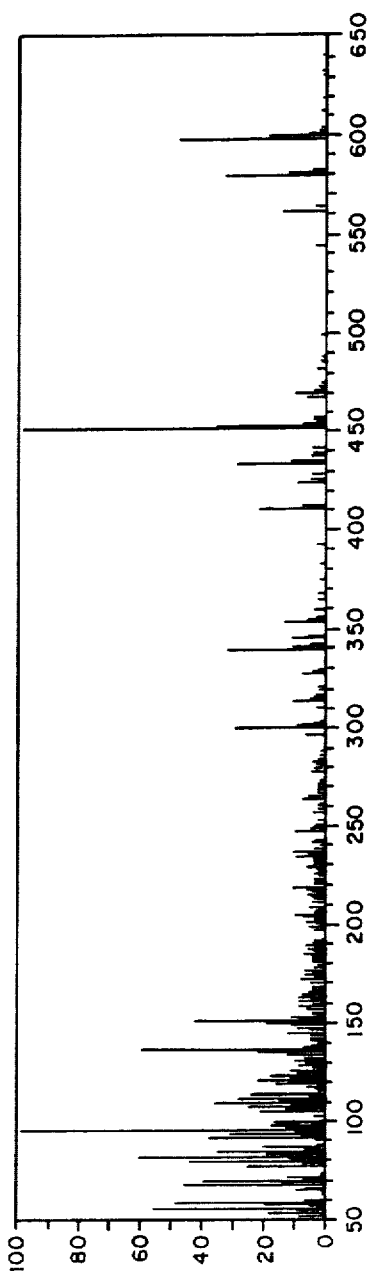
FIGURE XXV

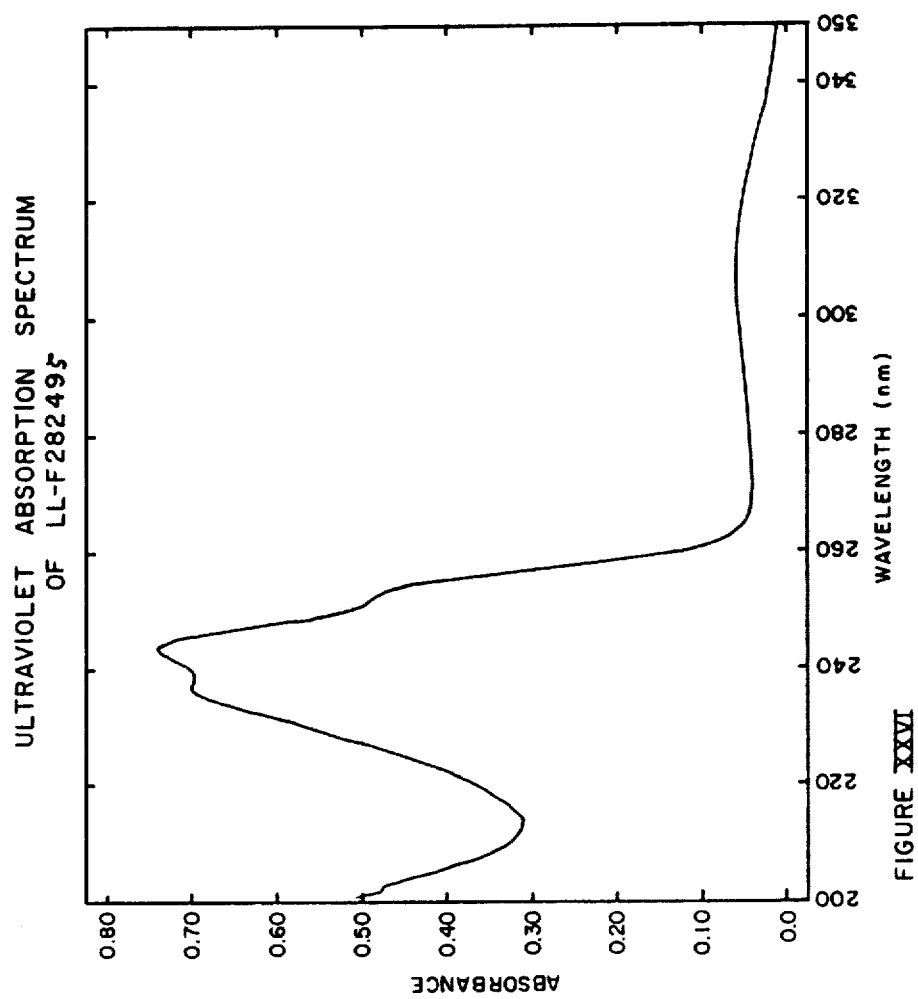

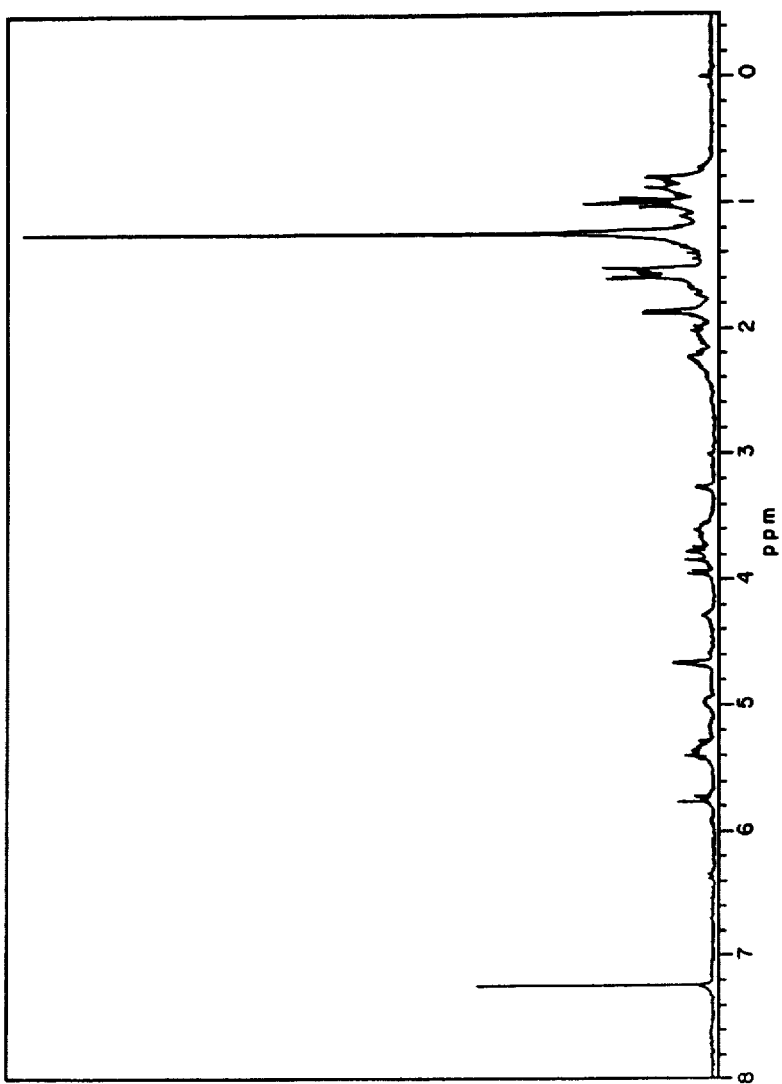
FIGURE XXXVII

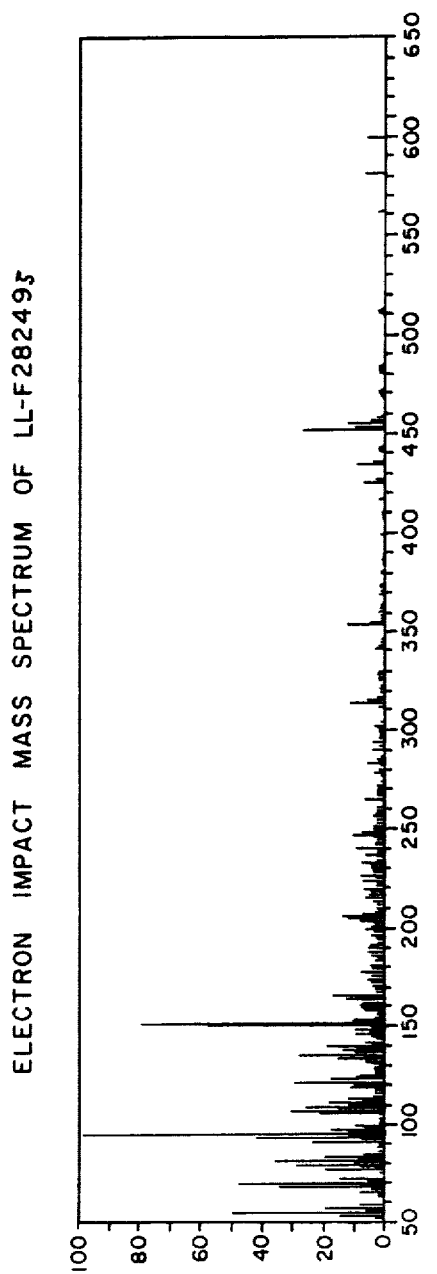

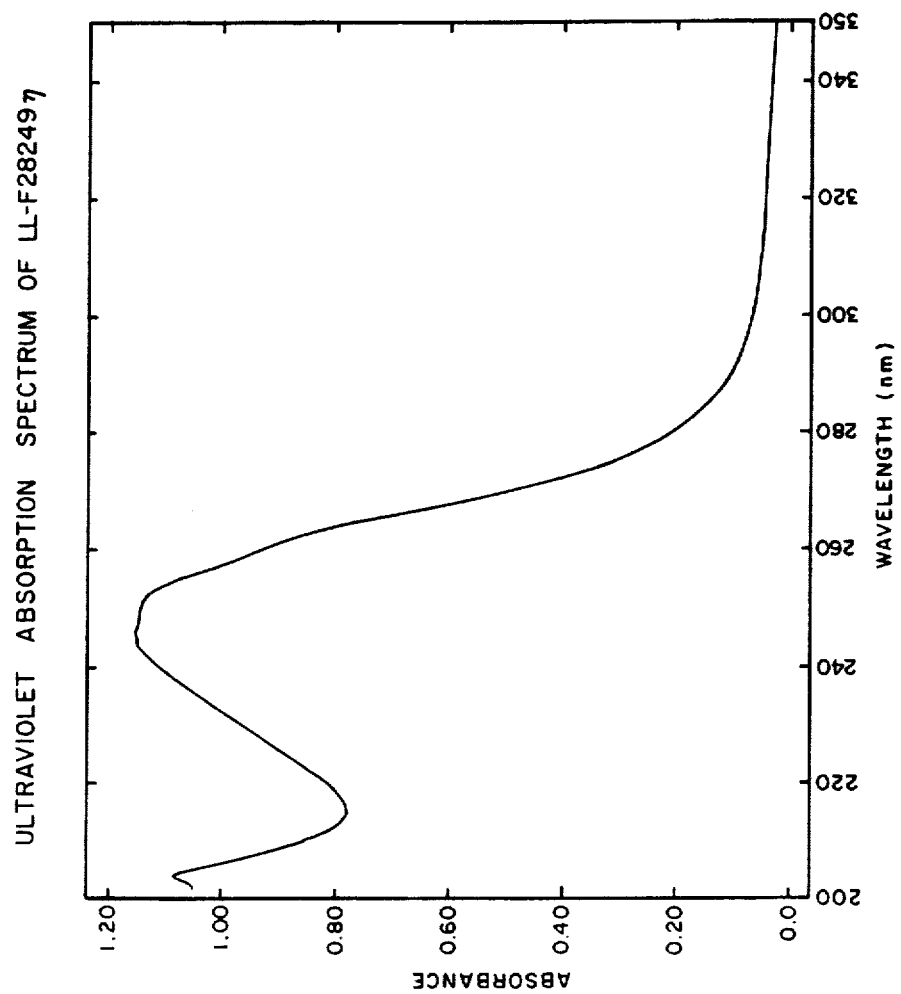
FIGURE XXIX

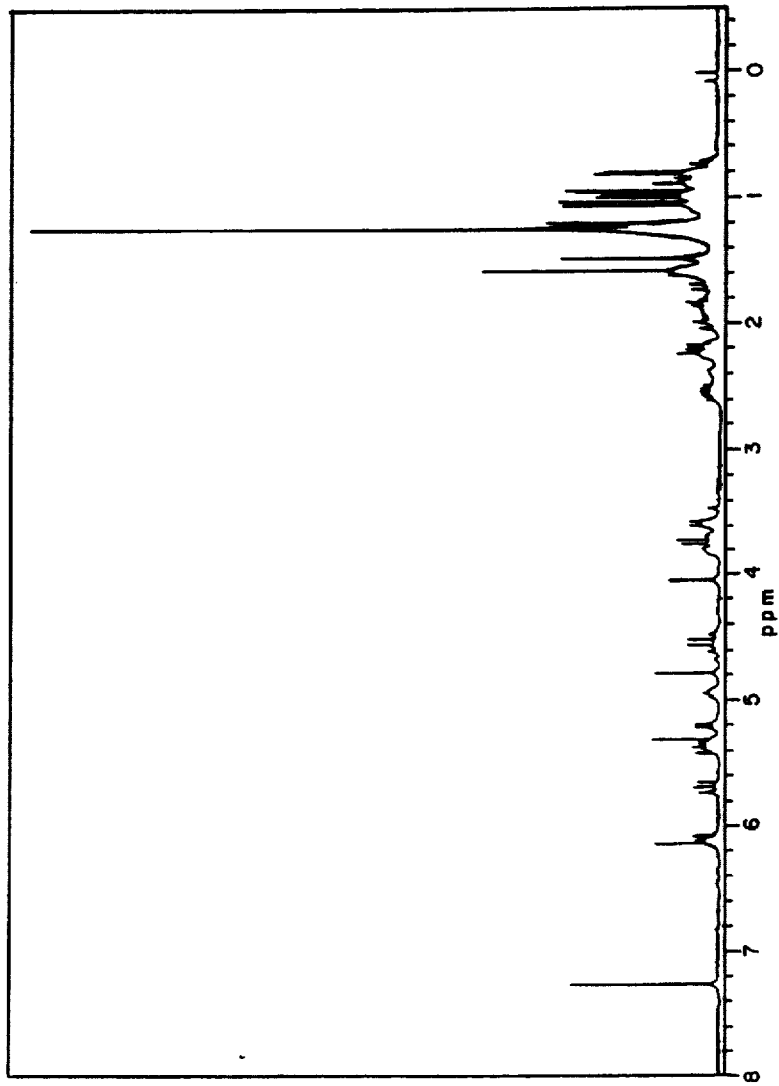
FIGURE XXX — PROTON NUCLEAR MAGNETIC RESONANCE SPECTRUM OF LL-F28249η IN CDCl₃ SOLUTION

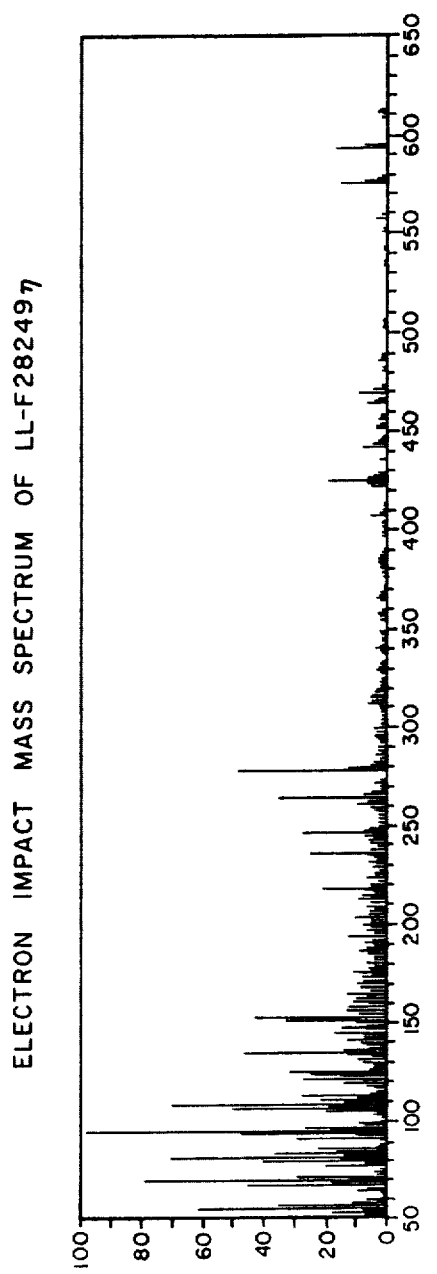
FIGURE XXXI

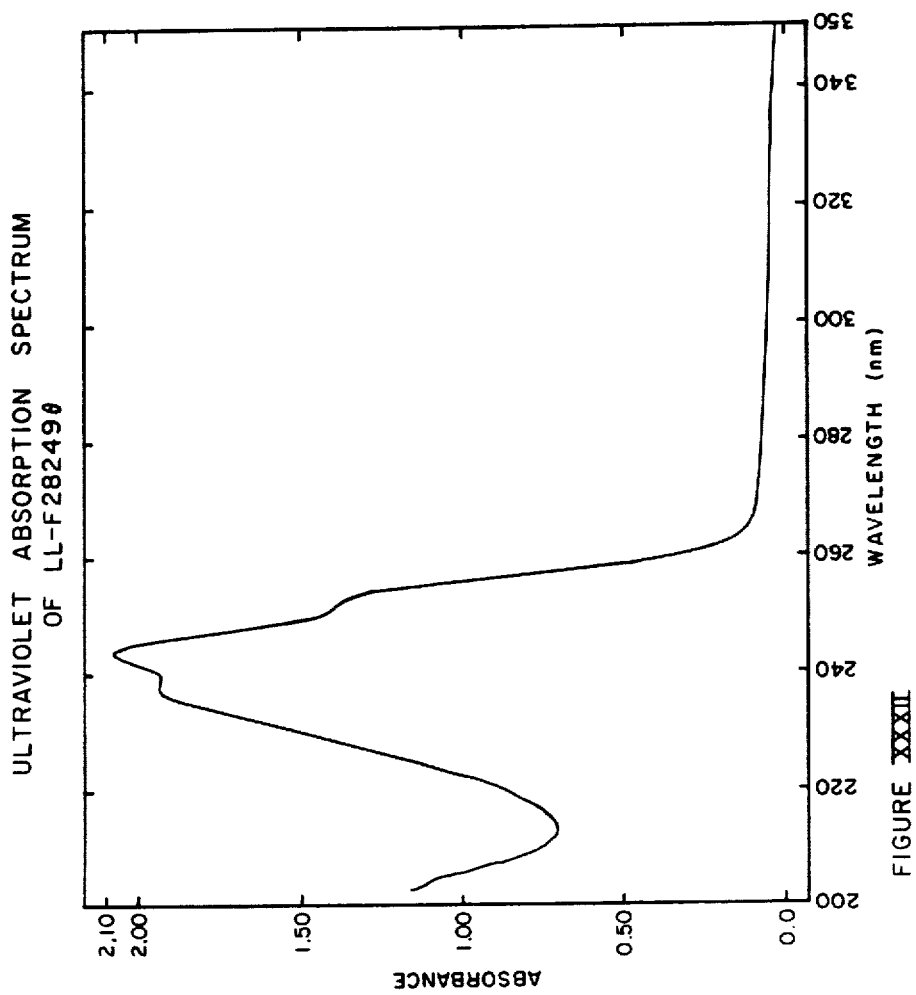
FIGURE XXXII

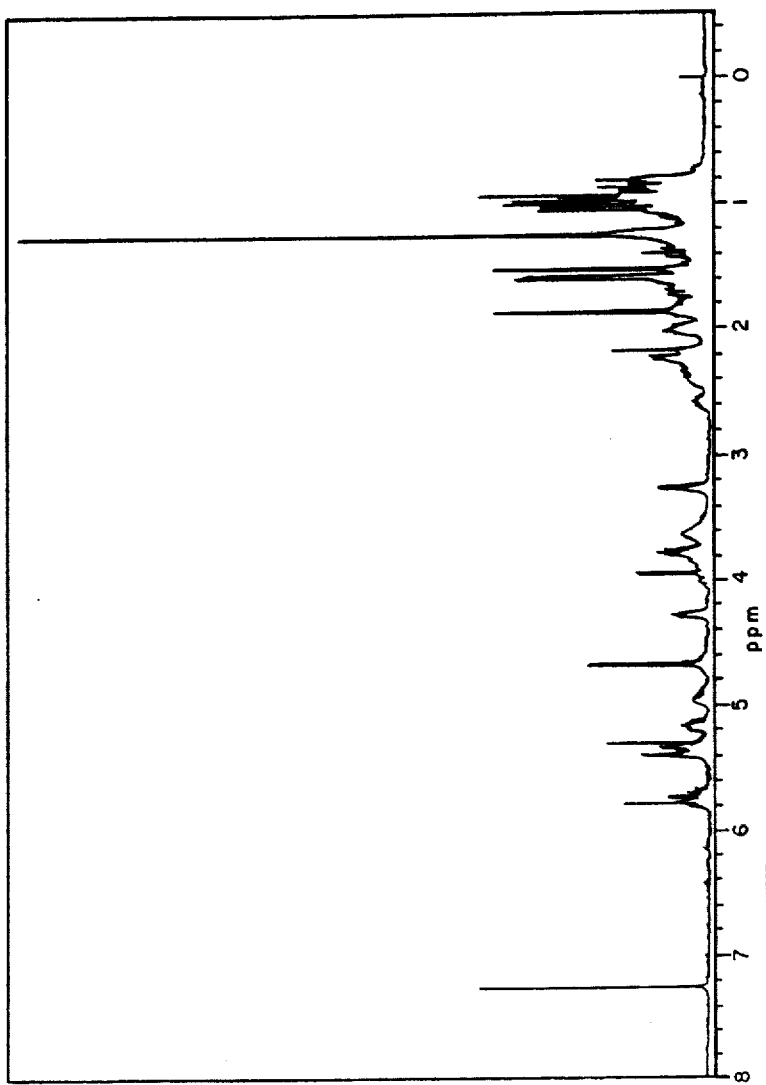
FIGURE XXXIII — PROTON NUCLEAR MAGNETIC RESONANCE SPECTRUM OF LL-F28249α IN CDCl₃ SOLUTION

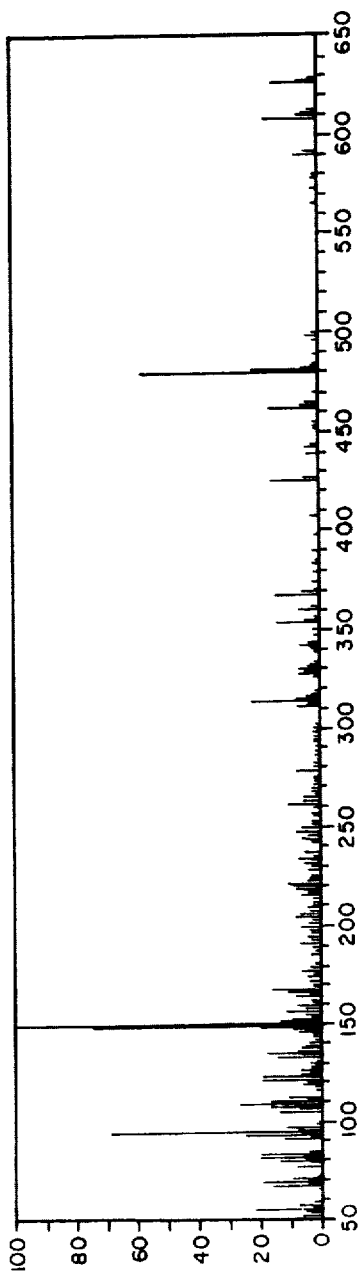
FIGURE XXXIV

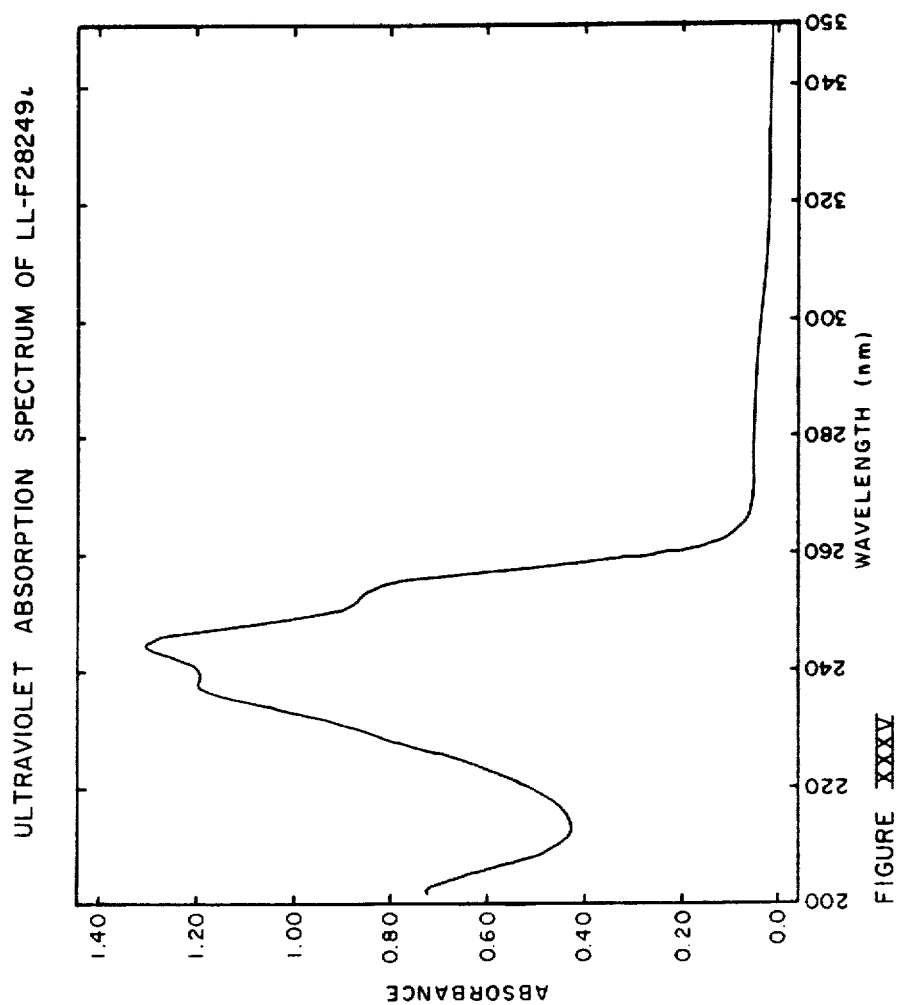
FIGURE XXXV

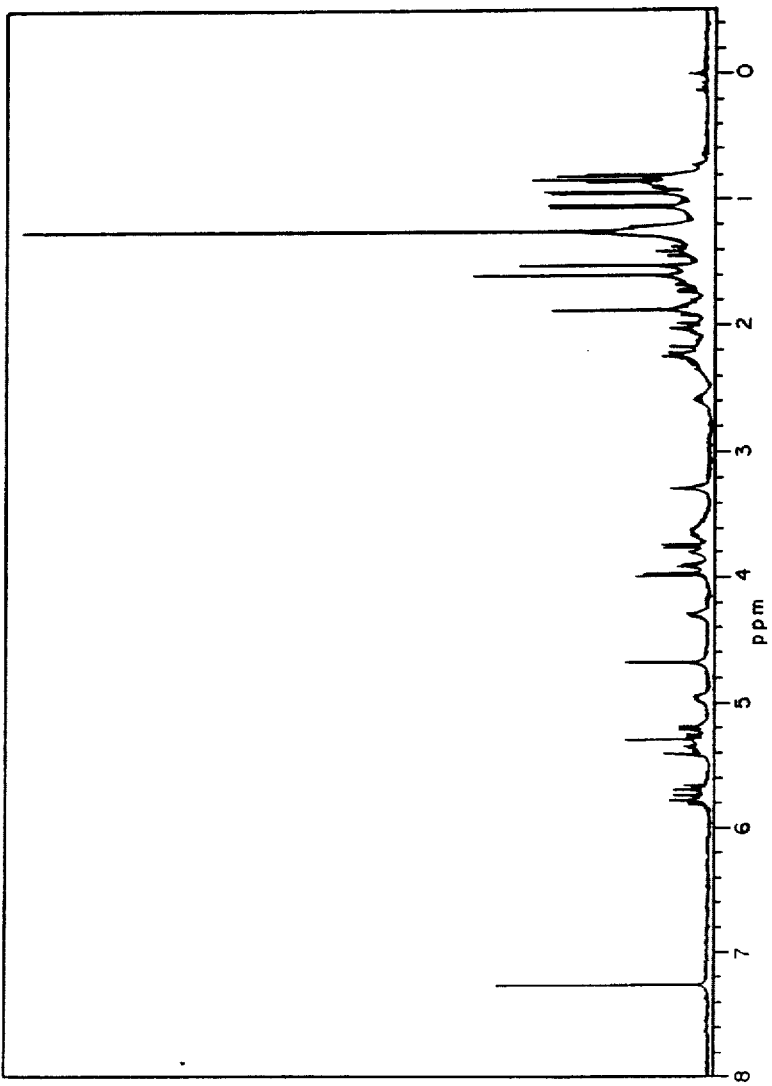
FIGURE XXXVI

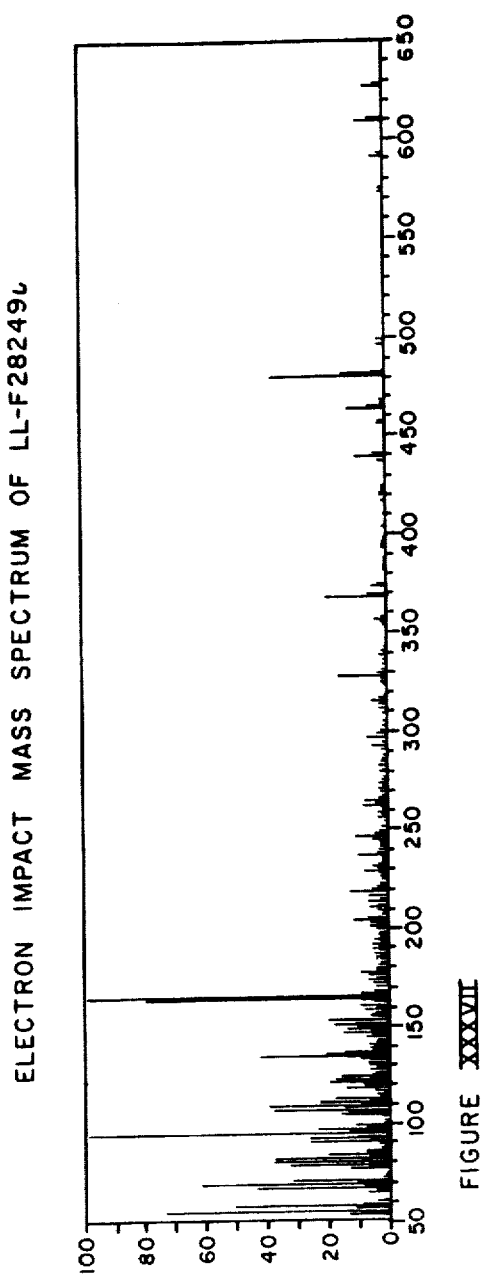

METHOD AND COMPOSITIONS FOR HELMINTIC, ARTHROPOD ECTOPARASITIC AND ACARIDAL INFECTIONS WITH NOVEL AGENTS

BACKGROUND OF THE INVENTION

The present invention relates to methods and compositions for preventing, treating or controlling helmintic, arthropod ectoparasitic and acaridal infections in warm-blooded animals by administering thereto an effective amount of the agents (compounds) designated LL-F28249α, β, γ, δ, ε, ζ, η, θ, ι and ω, or mixtures thereof, such as the fermentation broth or whole mash or the pharmaceutically and pharmacologically-acceptable salts thereof. Plant nematodes also are effectively controlled by use of these agents, mixtures and/or salts.

The diseases described above cause not only devastating effects but also serious economic problems and losses for farmers raising meat-producing animals such as swine, sheep, cattle, goats, rabbits, and poultry. Further, such diseases are a source of great concern for companion animals such as horses, dogs and cats. Although these diseases have been recognized for many years and drugs exist for the treatment and/or prevention of such diseases, the present invention utilizes an entirely new set of active agents, isolated from a previously unknown microorganism, for the prevention, treatment or control of those diseases.

For instance, U.S. Pat. No. 3,950,360, Aoki et al, Apr. 13, 1976, discloses certain antibiotic substances obtained by culturing a Streptomyces microorganism, said compounds being useful as insecticides and acaracides. But as seen from the characteristics identifying such microorganism, the present microorganism is distinct, and its active components are derived from totally different microorganism. Further, an entire series of U.S. patents relates to certain compounds produced by the fermentation of *Streptomyces avermitilis*, a distinct organism from the present one (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, June 3, 1980; U.S. Pat. No. 4,310,519, Albers-Schonberg, Jan. 12, 1982; U.S. Pat. No. 4,333,925, Buhs et al, June 8, 1982). U.S. Pat. No. 4,423,209, Mrozik, Dec. 27, 1983 relates to the process of converting some of these less desirable components to more preferred ones. However, the present active agents identified as LL-F28249α, β, γ, δ, ε, ζ, η, θ, ι and ω, are derived from the fermentation of a newly discovered and previously uncultivated microorganism. Also, the present compounds and/or the fermentation broth or whole mash of microorganism Streptomyces sp. LL-F28249, NRRL 15773, plus the pharmaceutically and pharmacologically-acceptable salts thereof (collectively referred to as active ingredient), exhibit excellent and effective treatments and/or prevention of these serious diseases of warm-blooded animals.

The full name of the microorganism LL-F28249, NRRL No. 15773, in terms of genus, species, and subspecies is *Streptomyces cyaneogriseus noncyanogenus*; however, for brevity it is named Streptomyces sp. throughout the specification and claims.

SUMMARY OF THE INVENTION

It is, therefore, an object of this invention to provide a novel method for the control of helmintic, arthropod ectoparastic and acaridal infections in warm-blooded animals, particularly meat-producing animals, such as poultry, cattle, sheep, swine, rabbits, and companion animals such as horses, dogs and cats.

It is also an object of the present invention to provide novel compositions effective for the control of said diseases in warm-blooded animals.

It has been discovered that the agents useful in the methods and compositions of the present invention are produced by the fermentation of a nutrient medium containing the strain of microorganism, Streptomyces sp. LL-F28249, NRRL 15773. These agents include not only the fermentation broth and whole mash of said microorganism but also include the agents, LL-F29249α, LL-F29249β, LL-F29249γ, LL-F29249δ, LL-F29249ε, LL-F29249ζ, LL-F29249η, LL-F29249θ, LL-F29249ι, and LL-F29249ω. These agents and methods for the preparation thereof are described in U.S. patent application of Guy Thomas Carter, Margaret Jennings Torrey and Michael Greenstein, Ser. No. 617,650, filed concurrently herewith and incorporated herein by reference thereto.

The structure and stereochemistry of LL-F28249α, β, γ and ω have not been fully defined, but the proposed such structures are as shown below. The structure and stereochemistry of LL-F28249δ, ε, ζ, η, θ, and ι have not been fully determined, but these compounds are closely related to LL-F28249α, β and γ, LL-F28249ω is related to Hondamycin (Albimycin), disclosed in The Journal of Antibiotics, 22 (11): 521–526 (1969).

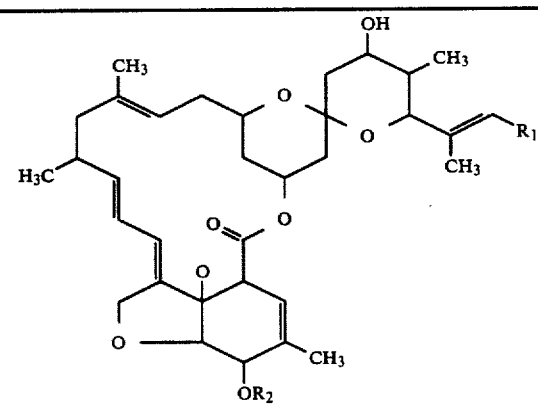

Component    R₁    R₂

|  |  |  |
|---|---|---|
| LL-F28249α | CH(CH₃)₂ | H |
| LL-F28249β | CH₃ | H |
| LL-F28249γ | CH₃ | CH₃ |

LL-F28249α, β, γ

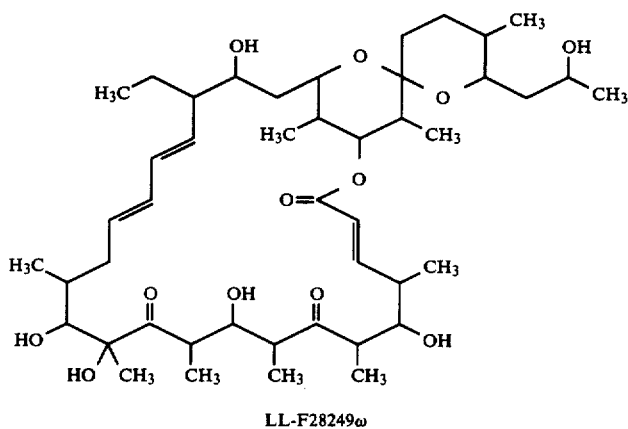

LL-F28249ω

DESCRIPTION OF THE DRAWINGS

FIG. 1: Characteristic ultraviolet absorption spectrum of compound designated LL-F28249α, NRRL 15773.

FIG. 2: Characteristic infrared absorption spectrum of compound designated LL-F28249α, NRRL 15773.

FIG. 3: Characteristic proton nuclear magnetic resonance spectrum of compound designated LL-F28249α, NRRL 15773, in CDCl₃ solution.

FIG. 4: Characteristic carbon-13 nuclear magnetic resonance spectrum of compound designated LL-F28249α, NRRL 15773, in CDCl₃ solution.

FIG. 5: Characteristic electron impact mass spectrum of compound designated LL-F28249α, NRRL 15773.

FIG. 6: Characteristic ultraviolet absorption spectrum of compound designated LL-F28249β, NRRL 15773.

FIG. 7: Characteristic infrared absorption spectrum of compound designated LL-F28249β, NRRL 15773.

FIG. 8: Characteristic proton nuclear magnetic resonance spectrum of compound designated LL-F28249β, NRRL 15773, in CDCl₃.

FIG. 9: Characteristic electron impact mass spectrum of compound designated LL-F28249β, NRRL 15773.

FIG. 10: Characteristic ultraviolet absorption spectrum of compound designated LL-F28249γ, NRRL 15773.

FIG. 11: Characteristic infrared absorption spectrum of compound LL-F28249γ, NRRL 15773.

FIG. 12: Characteristic proton nuclear magnetic resonance spectrum of compound LL-F28249γ, NRRL 15773, in CDCl₃.

FIG. 13: Characteristic carbon-13 nuclear magnetic resonance spectrum of compound designated LL-F28249γ, NRRL 15773, in CDCl₃.

FIG. 14: Characteristic electron impact mass spectrum of compound designated LL-F28249γ, NRRL 15773.

FIG. 15: Characteristic ultraviolet absorption spectrum of compound designated LL-F28249ω, NRRL 15773.

FIG. 16: Characteristic infrared absorption spectrum of compound designated LL-F28249ω, NRRL 15773.

FIG. 17: Characteristic proton nuclear magnetic resonance spectrum of compound designated LL-F28249ω, NRRL 15773, in CDCl₃.

FIG. 18: Characteristic nuclear magnetic resonance spectrum of compound designated LL-F28249ω, NRRl 15773, in CDCl₃.

FIG. 19: Characteristic electron impact mass spectrum of compound designated LL-F28249ω, NRRL 15773.

FIG. 20: Characteristic ultraviolet absorption spectrum of compound designated LL-F28249δ, NRRL 15773.

FIG. 21: Characteristic proton nuclear magnetic resonance spectrum of compound designated LL-F28249δ, NRRL 15773, in CDCl₃.

FIG. 22: Characteristic electron impact mass spectrum of compound designated LL-F28249δ, NRRL 15773.

FIG. 23: Characteristic ultraviolet absorption spectrum of compound designated LL-F28249ε, NRRL 15773.

FIG. 24: Characteristic proton nuclear magnetic resonance spectrum of compound designated LL-F28249ε, NRRL 15773, in CDCl₃.

FIG. 25: Characteristic electron impact mass spectrum of compound designated LL-F28249ε, NRRL 15773.

FIG. 26: Characteristic ultraviolet absorption spectrum of compound designated LL-F28249ζ, NRRL 15773.

FIG. 27: Characteristic proton nuclear magnetic resonance spectrum of compound designated LL-F28249ζ, NRRL 15773, in CDCl₃.

FIG. 28: Characteristic electron impact mass spectrum of compound designated LL-F28249ζ, NRRL 15773.

FIG. 29: Characteristic ultraviolet absorption spectrum of compound designated LL-F28249η, NRRL 15773.

FIG. 30: Characteristic proton nuclear magnetic resonance spectrum of compound designated LL-F28249η, NRRL 15773, in CDCl₃.

FIG. 31: Characteristic electron impact mass spectrum of compound designated LL-F28249η, NRRL 15773.

FIG. 32: Characteristic ultraviolet absorption spectrum of compound designated LL-F28249θ, NRRL 15773.

FIG. 33: Characteristic proton nuclear magnetic resonance spectrum of compound designated LL-F28249θ, NRRL 15773, in CDCl$_3$.

FIG. 34: Characteristic electron impact mass spectrum of compound designated LL-F28249θ, NRRL 15773.

FIG. 35: Characteristic ultraviolet absorption spectrum of compound designated LL-F28249ι, NRRL 15773.

FIG. 36: Characteristic proton nuclear magnetic resonance spectrum of compound designated LL-F28249ι, NRRL 15773, in CDCl$_3$.

FIG. 37: Characteristic electron impact mass spectrum of compound designated LL-F28249ι, NRRL 15773.

DETAILED DESCRIPTION OF THE INVENTION

It has been discovered that the above-mentioned agents, as well as the fermentation broth and whole mash of said microorganism, are especially effective for controlling helmintic, arthropod ectoparasitic and acaridal infections in meat-producing animals such as cattle, sheep, swine, rabbits, poultry, such as chickens, turkeys, ducks, geese, quail, and pheasants and companion animals.

In practice, the present invention involves the method of preventing, controlling or treating said infections, in warm-blooded animals by administering orgally, parentally, or topically thereto, a prophylactically, pharmaceutically or therapeuctically-effective amount of the fermentation broth or whole mash of microorganism Streptomyces species, LL-F28249, NRRL 15773, the fermentation broth or whole mash of said microogranism containing compounds designated LL-F28249α, β, γ, δ, ε, ζ, η, θ, ι and ω, compounds designated as LL-F28249α, LL-F28249β, LL-F28249γ, LL-F28249δ, LL-F28249ε, LL-F28249ζ, LL-F28249η, LL-F28249θ, LL-F28249ι, and LL-F28249ω, as identified and characterized herein, or the pharmaceutically and pharmacologically-acceptable salts thereof (collectively referred to as active ingredient).

Although administration of the compound or fermentation broth/whole mash (hereinafter broth or mash) will generally be most practical in or with the feed or in the drinking water, the above-said compounds, broth or mash, or pharmaceutically and pharmacologically-acceptable salts thereof, may also be administered to individual hosts in the form of tablets, drenches, gels, capsules, or the like, or by injection in the form of a paste, gel, pellet, or solution. These latter methods of administration are, of course, less practical for the treatment of large groups of animals, but they are quite practical for use on a small scale or on an individual basis.

When the agents (antibiotics) LL-F28249α, β, γ, δ, ε, ζ, η, θ, ι or ω or the fermentation broth or whole mash of Streptomyces sp. LL-F28249, NRRL 15773 are used as prophylactic or therapeutic treatments of helmintic, arthropod, ectoparasitic and acaridal infections, in animals and poultry, generally about 0.05 ppm to 500.0 ppm, and preferably 0.1 ppm to 300 ppm of the agent or broth or mash above-described, administered in the diet or drinking water of the animal, is effective for preventing, controlling, or treating said infections in those animals.

Medicated feeds useful in the method of the present invention are usually prepared by thoroughly admixing about 0.00001% by weight to about 0.01% by weight of the agent (antibiotic) or above-described broth or mash with a nutritionally-balanced feed, as for example, the feed described in the examples hereinafter.

When using the compounds and/or broth or mash of the present invention for the prevention or control of helminths, arthropod ectoparasites and acarides, the active agent is generally first prepared as an animal feed premix. The premix usually contains a relatively high percentage of the active ingredient and is generally blended with the animal's feed just prior to administration. If desired, the feed premix may also be applied as a top dressing for the animal's daily ration.

Feed premixes or concentrates, useful in the practice of the present invention, may be prepared by admixing about 0.1% to 5.0% by weight of the above-identified agents, broth or mash, or pharmaceutically and pharmacologically-acceptable salts thereof, with about 99.9% to 95% by weight of a suitable carrier or diluent.

Carriers suitable for use to make up the feed supplement compositions include the following: alfalfa meal, soybean meal, cottonseed oil meal, linseed oil meal, sodium chloride, calcium carbonate, calcium sulfate, cornmeal, cane molasses, urea, bone meal, corncob meal, rice hull meal, and the like. The carrier promotes an essentially uniform distribution of the active ingredient in the finished feed into which the supplement is blended. It thus performs an important function by ensuring proper distribution of the active ingredient, i.e., about 0.1 ppm to 100 ppm thereof, throughout the feed. This is equivalent to 0.00001% to 0.01%, by weight, of the active ingredient in the finished feed. In practice, usually one or more pounds of premix is added per ton of feed to obtain the desired level of agent (antibiotic) or broth or mash in the finished feed.

If the supplement or premix is used as a top dressing for feed, it likewise helps to ensure uniformity of distribution of the active ingredient across the top of the dressed feed.

Since the compounds of this invention and their pharmaceutically and pharmacologically-acceptable salts are relatively insoluble in water, it is generally desirable, when administering any such compound in the animal's drinking water, to dissolve the active ingredient in an organic solvent such as methanol, ethanol, acetone, DMSO, oleic acid, linoleic acid, propylene glycol, or the like, and admix with the solution a small amount of surfactant and/or dispersing agent to assure solution and/or dispersion of the active ingredient in the animal's drinking water.

Advantageously, where the treatment of a small number of the larger meat-producing animals is required to control parasitic infection therein, the agents LL-F28249α, β, γ, δ, ε, ζ, η, θ, ι and ω, broth or mash, or pharmaceutically or pharmacologically-acceptable salts thereof may be orally administered, on a daily basis, to the host animal in the form of a medicated gel.

The active ingredients of the invention have also exhibited nematocidal activity against plant nematodes as demonstrated by effectiveness in controlling the free living soil nematode, C. elegans. Compositions containing these active ingredients for controlling plant nematodes can be formulated into either liquids or wettable powders. Liquid compositions include about 5% to 20%, w/w, of the active ingredient (active agent, fermentation broth, whole mash or salts) with appropriate amounts of a solvent such as methanol, ethanol, acetone, acetonitrile, and others, and the remainder water. Wettable powders include about 5% to 20%, w/w, of the active ingredient, about 1% to 10% of surfactant, and inert carriers, such as clays, vermiculite, carbon black or the like. About 0.1 to 1.4 kg per hectare is applied to the foilage of plants, the soil in which they are grown or into the trunks thereof.

Surfactants useful in wettable powders of the present invention include those commonly used for formulations of such wettable powders, preferably alkylbenzene sulfonate sodium salts. Bentonite, clay or mixtures thereof are preferred carriers.

Additionally, the active ingredients of the invention also have demonstrated systemic insecticidal activity against *m. ovinus* in sheep.

In practice, generally about 0.02 mg/kg/day to about 3.0 mg/kg/day is effective for controlling parasitic infections in cattle, sheep, and swine and companion animals. For prolonged use, rates as low as 0.002 mg/kg of body weight/day may be employed.

Also in practice, about 0.1 mg per kg to 100 mg per kg is administered to animals infected with helminths.

The physicochemical characteristics for the $\alpha$, $\beta$, $\gamma$, $\delta$, $\epsilon$, $\zeta$, $\eta$, $\theta$, $\iota$ and $\omega$ components are described below:

LL-F28249$\alpha$:

(1) Molecular weight: 612 (FAB-MS);

(2) Molecular formula: $C_{36}H_{52}O_8$;

(3) Specific optical rotation: $[\alpha]_D^{26}=+133\pm3°$ (C 0.3, acetone):

(4) Ultraviolet absorption spectrum: as shown in FIG. I $UV_{MAX}^{CH3OH}=244$ nm ($\epsilon$28,000);

(5) Infrared absorption spectrum: as shown in FIG. II (KBr disc): 3439, 2960, 2925, 1714, 1454, 1374, 1338, 1171, 1120, 996, 967 $cm^{-1}$;

(6) Proton nuclear magnetic resonance spectrum ($CDCl_3$): as shown in FIG. III;

(7) Carbon-13 nuclear magnetic resonance spectrum ($CDCl_3$): as shown in FIG. IV and described in Table I; and (8) Electron impact mass spectrum: as shown in FIG. V with accurate mass measurements and proposed elemental compositions indicated in Table II.

LL-F28249$\beta$:

(1) Molecular weight: 584 (FAB-MS);

(2) Molecular formula: $C_{34}H_{48}O_8$;

(3) Ultraviolet absorption spectrum: as shown in FIG. VI $UV_{MAX}^{CH3OH}=244$ nm ($\epsilon$25,600);

(4) Infrared absorption spectrum: as shown in FIG. VII (KBr disc): 3520, 2910, 1735, 1717, 1450, 1375, 1335, 1180, 1170, 1119, 993, 727 $cm^{-1}$;

(5) Proton nuclear magnetic resonance spectrum ($CDCl_3$): as shown in FIG. VIII; and (6) Electron impact mass spectrum: as shown in FIG. IX with accurate mass measurements and proposed elemental compositions indicated in Table III.

LL-F28249$\gamma$:

(1) Molecular weight: 598 (FAB-MS);

(2) Molecular formula: $C_{35}H_{50}O_8$;

(3) Specific optical rotation: $[\alpha]_D^{26}=+150\pm4°$ (C 0.3, acetone);

(4) Ultraviolet absorption spectrum: as shown in FIG. X $UV_{MAX}^{CH3OH}=244$ nm ($\epsilon$27,100);

(5) Infrared absorption spectrum: as shown in FIG. XI (KBr disc): 3510, 2910, 1735, 1715, 1452, 1375, 1338, 1182, 1172, 1119, 995 $cm^{-1}$;

(6) Proton nuclear magnetic resonance spectrum ($CDCl_3$): as shown in FIG. XII;

(7) Carbon-13 nuclear magnetic resonance spectrum ($CDCl_3$): as shown in FIG. XIII and described in Table IV; and (8) Electron impact mass spectrum: as shown in FIG. XIV with accurate mass measurements and proposed elemental compositions indicated in Table V.

LL-F28249$\omega$:

(1) Molecular weight: 806 (FAB-MS);

(2) Molecular formula: $C_{45}H_{74}O_{12}$;

(3) Specific optical rotation: $[\alpha]_D^{26}=-49\pm3°$ (C 0.35, methanol);

(4) Ultraviolet absorption spectrum: as shown in FIG. XV $UV_{MAX}^{CH3OH}=225$ nm ($\epsilon$27,400), 232 nm ($\epsilon$25,700);

(5) Infrared absorption spectrum: as shown in FIG. XVI (KBr) disc): 3480, 2965, 2935, 2880, 1703, 1647, 1458, 1380, 1292, 1223, 1135, 1098, 984 $cm^{-1}$;

(6) Proton nuclear magnetic resonance spectrum ($CDCl_3$): as shown in FIG. XVII;

(7) Carbon-13 nuclear magnetic resonance spectrum ($CDCl_3$): as shown in FIG. XVIII and described in Table VI; and (8) Electron impact mass spectrum: as shown in FIG. XIX with accurate mass measurements and proposed elemental compositions indicated in Table VII.

LL-F28249$\delta$:

(1) HPLC retention volume of 14.0 ml in the system indicated in Table VIII;

(2) Ultraviolet absorption spectrum (methanol): as shown in FIG. XX;

(3) Proton nuclear magnetic resonance spectrum ($CDCL_3$): as shown in FIG. XXI; and (4) Electron impact mass spectrum: as shown in FIG. XXII.

LL-F28249$\epsilon$:

(1) HPLC retention volume of 14.8 ml in the system indicated in Table VIII;

(2) Ultraviolet absorption spectrum (methanol): as shown in FIG. XXIII;

(3) Proton nuclear magnetic resonance spectrum ($CDCl_3$): as shown in FIG. XXIV; and (4) Electron impact mass spectrum: as shown in FIG. XXV.

LL-F28249$\zeta$:

(1) HPLC retention volume of 16.0 ml in the system indicated in Table VIII;

(2) Ultraviolet absorption spectrum (methanol): as shown in FIG. XXVI;

(3) Proton nuclear magnetic resonance spectrum ($CDCL_3$): as shown in FIG. XXVII; and (4) Electron impact mass spectrum: as shown in FIG. XXVIII.

LL-F28249$\eta$:

(1) HPLC retention volume of 23.5 ml in the system indicated in Table VIII;

(2) Ultraviolet absorption spectrum (methanol): as shown in FIG. XXIX;

(3) Proton nuclear magnetic resonance spectrum ($CDCl_3$): as shown in FIG. XXX; and (4) Electron impact mass spectrum: as shown in FIG. XXXI.

LL-F28249$\theta$:

(1) HPLC retention volume of 24.5 ml in the system indicated in Table VIII;

(2) Ultraviolet absorption spectrum (methanol): as shown in FIG. XXXII;

(3) Proton nuclear magnetic resonance spectrum ($CDCl_3$): as shown in FIG. XXXIII; and (4) Electron impact mass spectrum: as shown in FIG. XXXIV.

LL-F28249ι:

(1) HPLC retention volume of 26.0 ml in the system indicated in Table VIII;

(2) Ultraviolet absorption spectrum (methanol): as shown in FIG. XXXV;

(3) Proton nuclear magnetic resonance spectrum ($CDCl_3$): as shown in FIG. XXXVI; and (4) Electron impact mass spectrum: as shown in FIG. XXXVII.

TABLE I

Carbon-13 NMR Data for LL-F28249α

| Carbon | Chemical Shift[1] (ppm) | Proton Substitution | Carbon | Chemical Shift (ppm) | Proton Substitution |
|---|---|---|---|---|---|
| 1 | 173.4 | q[2] | 18 | 67.8 | CH |
| 2 | 142.8 | CH | 19 | 67.7 | CH |
| 3 | 139.4 | q | 20 | 48.4 | $CH_2$ |
| 4 | 137.7 | q | 21 | 45.7 | CH |
| 5 | 137.3 | q | 22 | 41.1 | $CH_2$ |
| 6 | 137.2 | CH | 23 | 40.7 | $CH_2$ |
| 7 | 130.6 | q | 24 | 36.1 | $CH_2$ |
| 8 | 123.3 | CH | 25 | 36.0 | CH |
| 9 | 120.3[3] | CH | 26 | 35.9 | CH |
| 10 | 118.0 | CH | 27 | 34.7 | $CH_2$ |
| 11 | 99.7 | q | 28 | 26.8 | CH |
| 12 | 80.2 | q | 29 | 22.8[4] | $CH_3$ |
| 13 | 79.3 | CH | 30 | 22.2 | $CH_3$ |
| 14 | 76.7 | CH | 31 | 19.9 | $CH_3$ |
| 15 | 69.3 | CH | 32 | 15.5 | $CH_3$ |
| 16 | 68.5 | CH | 33 | 13.9 | $CH_3$ |
| 17 | 68.4 | $CH_2$ | 34 | 11.0 | $CH_3$ |

[1]Downfield from TMS; $CDCl_3$ solution.
[2]q = quaternary carbon.
[3,4]Two unresolved signals.

TABLE II

High Resolution Mass Measurements for LL-F28249α

| m/z | Elemental Composition |
|---|---|
| 612.3705 | $C_{36}H_{52}O_8$ |
| 594.3543 | $C_{36}H_{50}O_7$ |
| 576.3472 | $C_{36}H_{48}O_6$ |
| 484.3211 | $C_{30}H_{44}O_5$ |
| 482.2648 | $C_{29}H_{38}O_6$ |
| 466.3097 | $C_{30}H_{42}O_4$ |
| 448.2987 | $C_{30}H_{40}O_3$ |
| 442.2375 | $C_{26}H_{34}O_6$ |
| 425.2327 | $C_{26}H_{33}O_5$ |
| 354.2181 | $C_{23}H_{30}O_3$ |
| 314.1877 | $C_{20}H_{26}O_3$ |
| 278.1144 | $C_{15}H_{18}O_5$ |
| 265.1786 | $C_{16}H_{25}O_3$ |
| 248.1405 | $C_{15}H_{20}O_3$ |
| 247.1705 | $C_{16}H_{23}O_2$ |
| 237.1838 | $C_{15}H_{25}O_2$ |
| 219.1740 | $C_{15}H_{23}O$ |
| 151.0753 | $C_9H_{11}O_2$ |

TABLE III

High Resolution Mass Measurements for LL-F28249β

| m/z | Elemental Composition |
|---|---|
| 584.3388 | $C_{34}H_{48}O_8$ |
| 566.3306 | $C_{34}H_{46}O_7$ |
| 456.2864 | $C_{28}H_{40}O_5$ |
| 442.2391 | $C_{26}H_{34}O_6$ |
| 438.2780 | $C_{28}H_{38}O_4$ |
| 425.2331 | $C_{26}H_{33}O_5$ |
| 354.2187 | $C_{23}H_{30}O_3$ |
| 314.1858 | $C_{20}H_{26}O_3$ |
| 278.1168 | $C_{15}H_{18}O_5$ |
| 237.1491 | $C_{14}H_{21}O_3$ |
| 219.1380 | $C_{14}H_{19}O_2$ |
| 209.1534 | $C_{13}H_{21}O_2$ |
| 191.1418 | $C_{13}H_{19}O$ |
| 151.0750 | $C_9H_{11}O_2$ |

TABLE IV

Carbon-13 NMR Data for LL-F28249γ

| Carbon | Chemical Shift[1] (ppm) | Carbon | Chemical Shift (ppm) |
|---|---|---|---|
| 1 | 173.6 | 18 | 68.3 |
| 2 | 142.4 | 19 | 67.9 |
| 3 | 139.9 | 20 | 57.7 |
| 4 | 137.3 | 21 | 48.5 |
| 5 | 136.0 | 22 | 45.8 |
| 6 | 134.0 | 23 | 41.2 |
| 7 | 123.8 | 24 | 40.8 |
| 8 | 123.6 | 25 | 36.2 |
| 9 | 120.4 | 26 | 36.1 |
| 10 | 119.6 | 27 | 36.0[2] |
| 11 | 118.5 | 28 | 34.8 |
| 12 | 99.8 | 29 | 22.3 |
| 13 | 80.5 | 30 | 19.9 |
| 14 | 77.8 | 31 | 15.5 |
| 15 | 76.8 | 32 | 13.8 |
| 16 | 69.3 | 33 | 13.1 |
| 17 | 68.6 | 34 | 10.8 |

[1]Downfield from TMS; $CDCl_3$ solution.
[2]Two unresolved signals.

TABLE V

High Resolution Mass Measurements for LL-F28249γ

| m/z | Elemental Composition |
|---|---|
| 598.3543 | $C_{35}H_{50}O_8$ |
| 580.3422 | $C_{35}H_{48}O_7$ |
| 562.3292 | $C_{35}H_{46}O_6$ |
| 496.2824 | $C_{30}H_{40}O_6$ |
| 484.2440 | $C_{28}H_{36}O_7$ |
| 478.2687 | $C_{30}H_{38}O_5$ |
| 456.2576 | $C_{27}H_{36}O_6$ |
| 438.2772 | $C_{28}H_{38}O_4$ |
| 425.2341 | $C_{26}H_{33}O_5$ |
| 420.2651 | $C_{28}H_{36}O_3$ |
| 354.2199 | $C_{23}H_{30}O_3$ |
| 314.1875 | $C_{20}H_{26}O_3$ |
| 292.1307 | $C_{16}H_{20}O_5$ |
| 288.2075 | $C_{19}H_{28}O_2$ |
| 248.1397 | $C_{15}H_{20}O_3$ |
| 237.1490 | $C_{14}H_{21}O_3$ |
| 219.1382 | $C_{14}H_{19}O_2$ |
| 209.1544 | $C_{13}H_{21}O_2$ |
| 191.1435 | $C_{13}H_{19}O$ |
| 151.0759 | $C_9H_{11}O_2$ |

TABLE VI

Carbon-13 NMR Data for LL-F28249ω

| Carbon | Chemical Shift[1] (ppm) | Carbon | Chemical Shift (ppm) |
|---|---|---|---|
| 1 | 220.7 | 23 | 42.2[2] |
| 2 | 219.6 | 24 | 40.4 |
| 3 | 165.2 | 25 | 38.3 |
| 4 | 148.7 | 26 | 37.6 |
| 5 | 133.1 | 27 | 36.1 |

TABLE VI-continued

Carbon-13 NMR Data for LL-F28249ω

| Carbon | Chemical Shift[1] (ppm) | Carbon | Chemical Shift (ppm) |
|---|---|---|---|
| 6 | 132.3 | 28 | 34.8 |
| 7 | 132.1 | 29 | 33.5 |
| 8 | 130.2 | 30 | 30.1 |
| 9 | 122.3 | 31 | 26.6 |
| 10 | 100.0 | 32 | 25.4 |
| 11 | 82.9 | 33 | 24.5 |
| 12 | 75.9 | 34 | 23.0 |
| 13 | 73.0 | 35 | 21.1 |
| 14 | 72.7 | 36 | 17.9 |
| 15 | 72.6 | 37 | 14.3 |
| 16 | 72.1 | 38 | 14.2 |
| 17 | 69.0 | 39 | 12.1 |
| 18 | 67.3 | 40 | 11.5 |
| 19 | 63.6 | 41 | 10.9 |
| 20 | 51.4 | 42 | 8.7 |
| 21 | 46.2 | 43 | 8.3 |
| 22 | 45.7 | 44 | 5.7 |

[1] Downfield from TMS; CDCl$_3$ solution.
[2] Two unresolved signals.

TABLE VII

High Resolution Mass Measurements for LL-F28249ω

| m/z | Elemental Composition |
|---|---|
| 462.3350 | $C_{28}H_{46}O_5$ |
| 444.3237 | $C_{28}H_{44}O_4$ |
| 425.2534 | $C_{23}H_{37}O_7$ |
| 407.2439 | $C_{23}H_{35}O_6$ |
| 406.3046 | $C_{25}H_{42}O_4$ |
| 387.2895 | $C_{25}H_{39}O_3$ |
| 337.2010 | $C_{19}H_{29}O_5$ |
| 297.2031 | $C_{17}H_{29}O_4$ |
| 279.1944 | $C_{17}H_{27}O_3$ |
| 261.1851 | $C_{17}H_{25}O_2$ |
| 253.1797 | $C_{15}H_{25}O_3$ |
| 235.1697 | $C_{15}H_{23}O_2$ |
| 224.1754 | $C_{14}H_{24}O_2$ |
| 209.1530 | $C_{13}H_{21}O_2$ |
| 207.1744 | $C_{14}H_{23}O$ |
| 184.1458 | $C_{11}H_{20}O_2$ |
| 179.1048 | $C_{11}H_{15}O_2$ |
| 173.1205 | $C_9H_{17}O_3$ |
| 167.1051 | $C_{10}H_{15}O_2$ |
| 155.1069 | $C_9H_{15}O_2$ |

TABLE VIII

HPLC Retention Volumes for LL-F28249α, δ, ε, ζ, η, θ and ι

| Compound | Retention Volume*(ml) |
|---|---|
| LL-F28249α | 19.8 |
| LL-F28249δ | 14.0 |
| LL-F28249ε | 14.8 |
| LL-F28249ζ | 16.0 |
| LL-F28249η | 23.5 |
| LL-F28249θ | 24.5 |
| LL-F28249ι | 26.0 |

*System includes a column 3.9 mm × 30 cm packed with C$_{18}$ reverse phase packing developed with methanol:water (80:20) at 1.0 ml/minute, detection was by absorbance at 254 nm.

The new agents designated LL-F28249α, β, γ, δ, ε, ζ, η, θ, ι and ω are formed during the cultivation, under controlled conditions of Streptomyces sp. LL-F28249, NRRL 15773.

This organism is maintained in the culture collection of the Medical Research Division, American Cyanamid Company, Pearl River N.Y. as culture number LL-F28249. A viable culture of this new microorganism has been deposited with the Patent Culture Collection Laboratory, Northern Regional Research Center, U.S. Department of Agriculture, Peoria, Ill. 61604, and has been added to its permanent collection. It is freely available to the public in this depository under its accession number NRRL 15773.

For the production of these new agents the present invention is not limited to this particular organism. In fact, it is desired and intended to include the use of naturally-occurring mutants of this organism, as well as induced mutants produced from this organism by various mutagenic means known to those skilled in the art, such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techiques known to those skilled in the art such as for example, conjugation, transduction and genetic engineering techniques.

General Fermentation Conditions

Cultivation of Streptomyces sp. LL-F28249, NRRL 15773 may be carried out in a wide variety of liquid culture media. Media which are useful for the production of agents LL-F28249α, β, γ, δ, ε, ζ, η, θ, ι and ω include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

EXAMPLE 1

Inoculum Preparation

A typical medium used to grow the various stages of inoculum was prepared according to the following formula:

| | |
|---|---|
| Dextrose | 1.0% |
| Dextrin | 2.0% |
| Yeast extract | 0.5% |
| NZ amine | 0.5% |
| Calcium carbonate | 0.1% |
| Water qs | 100% |

This medium was sterilized. A 100 ml portion of this sterile medium, in a flask, was inoculated with mycelial scrapings from an agar slant of Streptomyces sp. LL-F28249, NRRL 15773. The medium was then agitated vigorously on a rotary shaker for 48-72 hours at 28° C. providing primary inoculum. This primary inoculum was then used to inoculate one liter of the above sterile medium, which was then grown aerobically at 28° C. for 48 hours providing secondary inoculum.

EXAMPLE 2

Fermentation

A fermentation medium of the following formulation was prepared.

| | |
|---|---|
| Dextrin | 1.0% |
| Soya peptone | 1.0% |

-continued

| | |
|---|---|
| Molasses | 2.0% |
| Calcium carbonate | 0.1% |
| Water qs | 100% |

This medium was sterilized and then a 30 liter portion was inoculated with one liter of secondary inoculum prepared as described in Example 1. The fermentation was conducted at 30° C., with a sterile air flow of 30 liters per minute, backpressure of 8 psig and agitation by an impeller operated at 500 rpm for 91 hours at which time the mash was harvested.

EXAMPLE 3

Isolation of LL-F28249α, β and γ

A total of 26 liters of whole harvest mash, prepared as described in Example 2 was mixed with 1500 g of diatomaceous earth and filtered. The mycelial cake was washed with 5 liters of water and the filtrate and wash discarded. The mycelial cake was mixed with 10 liters of methanol for one hour, then filtered and washed with 5 liters of methanol. The methanol extract and methanol wash were combined and evaporated to an aqueous residue of about 1-2 liters. This aqueous residue was mixed with twice its volume of methylene chloride and mixed for ½ hour. The methylene chloride phase was separated and then concentrated to a syrup giving 27 g of crude material.

This 27 g of crude material was dissolved in a mixture of methylene chloride and methanol, filtered through cotton and anhydrous sodium sulfate and then evaporated, giving 7.0 g of an oil.

A 170 g portion of silica gel was slurried in 12.5% ethyl acetate in methylene chloride and poured to form a column 2.5×58 cm. The oil was dissolved in 12.5% ethyl acetate in methylene chloride and applied to the column. The column was developed with the same solvent mixture. The mobile phase was run at 1.3 ml/minute initially and 15 minute fractions were collected. The flow rate slowed to about 0.5 ml/minute after 10 fractions, so fractions 1–10 were 20 ml decreasing to about 10 ml uniformly and fractions 11–98 were about 7 ml. At fraction 99 the flow rate was increased to give 25 ml fractions in 10 minutes. A total of 105 fractions were collected. These fractions were tested by thin layer chromatography in ethyl acetate:methylene chloride (1:1).

Fractions 30–54 were combined and evaporated giving 1.08 g of an oil containing LL-F28249γ.

Fractions 55–62 were combined and evaporated giving 150 mg of solid containing LL-F28249α and β.

The 150 mg of solid containing LL-F28249α and β was chromatographed by preparative HPLC using a reverse-phase column (Whatman C8, 2.2×50 cm) developed with 80% (v/v) methanol in water. The flow rate was about 10 ml/minute and 2 minute fractions were collected.

Fractions 58–69 were combined, the methanol was evaporated, t-butanol was added and the mixture was lyophilized, giving 60 mg of pure LL-F28249α.

Fractions 40–43 were combined, the methanol was evaporated and the residual aqueous suspension was extracted with methylene chloride which, upon evaporation, gave 10 mg of pure LL-F28249β.

The 1.08 g of oil containing LL-F28249γ was dissolved in 10% ethyl acetate in methylene chloride and applied to a column (2.5×50 cm) packed with silica gel. The column was developed with 10% ethyl acetate in methylene chloride, eluting at a flow rate of 2 ml/minute and collecting 12 minute fractions. Fractions 19–29 were combined and evaporated to a residue. This residue was purified by preparative reverse-phase chromatography as described for the α and β components. Fractions 55–62 were combined, the methanol was evaporated in vacuo, t-butanol was added and the mixture was lyophilized giving 60 mg of pure LL-F28249γ.

EXAMPLE 4

Large Scale Ferementation

An inoculum of Streptomyces sp. LL-F28249, NRRL 15773 was prepared as described in Example 1, using 100 ml of primary inoculum to produce 10 liters of secondary inoculum.

Two 300 liter fermentations were conducted as described in Example 2 using 10 liters of the above secondary inoculum for each 300 liters of fermentation medium. At the end of 118 hours the mashes were harvested.

EXAMPLE 5

Isolation of LL-F28249ω

A total of 450 liters of harvest mash from the two 300 liter fermentations described in Example 4 was treated as described in the first portion of Example 3 giving crude material as a syrup.

This syrupy residue was washed with hexane to remove non-polar materials and the remaining 9 g of insoluble material was subjected to Sephadex LH-20 partition chromatography.

The chromatographic column was prepared with 9 liters of Sephadex LH-20, previously swelled in methanol, to form a column 10×110 cm. The column was equilibrated by passing about 4800 ml of mobile phase [methylene chloride:hexane:methanol (10:10:1)] through it at a flow rate of 5 ml/minute. The 9 g of insoluble material was charged onto the column in 50 ml of the mobile phase. An initial forerun of 2150 ml was obtained at a flow rate of 5 ml/minute. The flow rate was then increased to 8 ml/minute and fractions were collected every 45 minutes. Fractions 9–12 were combined and the solvents evaporated in vacuo giving 4.9 g of residue.

This residue was dissolved in a 1:1 mixture of cyclohexane and ethyl acetate and allowed to evaporate slowly at room temperature. The addition of n-hexane gave a precipitate which was collected, giving 3.1 g of solid.

A 3.0 g portion of this solid was further purified by precipitation from 25 ml of methylene chloride using 50 ml of n-hexane.

The precipitate thus obtained was redissolved in 15 ml of methylene chloride and precipitated with 25 ml of n-hexane, giving 510 mg of pure LL-F28249ω.

EXAMPLE 6

Isolation of LL-F28249δ, ε, ζ, η, θ and ι

Fractions 4–7 from the Sephadex LH-20 column described in Example 5 were combined and the solvents evaporated in vacuo to give 1.9 g of residue.

The residue was chromatographed on a 200 g silica gel column (2.5 cm×83 cm) using 10% ethyl acetate in methylene chloride as the eluant. The flow rate was approximately 2 ml/minute and fractions were collected every 12 minutes.

Fractions 65-67 and 73-79 were combined together and the solvents were evaporated in vacuo to yield 250 mg of residue.

This 250 mg of residue was subjected to preparative reverse-phase chromatography as described in Example 3 except using 75% methanol in water as the mobile phase. The flow rate was about 10 ml/minute. The first 2000 ml portion of eluate was diverted to waste then 72 fractions were collected at 2.0 minute intervals. After diverting another portion of eluate to waste (between 300-400 ml) fractions were collected again but at 2.5 minute intervals.

Fractions were combined as indicated below. The combined fractions were allowable to evaporate in a fume hood overnight, then the components were extracted into methylene chloride. Following evaporation of the solvent about 1 mg each of the pure components were obtained.

| Fractions Combined | Compound |
|---|---|
| 7-10 | LL-F28249δ |
| 19-22 | LL-F28249ε |
| 28-31 | LL-F28249ζ |
| 81-83 | LL-F28249η |
| 86-88 | LL-F28249θ |
| 93-95 | LL-F28249ι |

EXAMPLE 7
Anti-nematodal activity of LL-F28249, NRRL 15773

This in vitro assay is designed to utilize the free living nematode *Caenorhabditis elegans* (*C. elegans*) to detect the anti-nematodal activity of fermentation broths against microorganisms from the soil. The assay procedure consists of micropipetting 50 μl of each broth into one of 96 wells of a microculture plate and adding 10 μl of a three to four day-old culture of *C. elegans* (in all stages of development) suspended in *C. briggsae* Maintenance Medium. The effects of the fermentation broths are observed and recorded at 48 hours after the initial mixing of broth and nematodes.

LL-F28249, NRRL 15773, broth killed all the adults and markedly reduced the survival and mobility of various larval stages in both the initial and in a replicate assay.

EXAMPLE 8
In vivo anthelmintic activity of LL-F28249, NRRL 15773

This in vivo system is designed to detect potential anthelmintic activity of all fermentation products found to have anti-nematodal action against *C. elegans*. Samples of LL-F28249, NRRL 15773 are mixed into feed, at concentrations of from 0.0031% to 2.0% (31 ppm to 20,000 ppm). Medicated diet containing the varying concentrations of LL-F28249, NRRL 15773 is given to gerbils infected with 400 third-stage larvae of *Trichostrongylus colubriformis*. The medicated feed is fed ad libitum, starting when the infection is seven days old, for three and one-half to four days, at which time the gerbils are necropsied. The intestines are removed and placed in water in an incubator at 45° C. for two hours to allow the parasites to migrate from the tissue. The efficacy of each treatment is determined by counting the number of *T. colubriformis* recovered compared to an untreated control. The results of these experiments, summarized in Table IX below, demonstrate the anthelmintic activity of LL-F28249 as administered in feed, and when administered as a single oral drench, and by subcutaneous injection.

TABLE IX

Anthelmintic activity of active ingredients from LL-F28249, NRRL 15773 culture against *Trichostrongylus colubriformis* in the gerbil

| F28249 | With medicated diet, Ad libitum | | | | |
|---|---|---|---|---|---|
| Whole mash (lyophilized) | Conc. (ppm) | 500.0 | 250.0 | 125.0 | 62.5 |
| | Efficacy % | 100.0 | 98.0 | 88.0 | 40.0 |
| α | Conc. (ppm) | 20.0 | 0.5 | 0.1 | 0.05 |
| | Efficacy % | 100.0 | 100.0 | 97.0 | 31.0 |
| | With single oral drench | | | | |
| Whole Mash (lyophilized) | Dose (mg/kg) | 200.0 | 100.0 | 50.0 | 25.0 |
| | Efficacy % | 100.0 | 100.0 | 100.0 | 88.0 |
| α | Dose (mg/kg) | 10.0 | 0.5 | 0.1 | 0.05 | 0.025 |
| | Efficacy % | 100.0 | 100.0 | 100.0 | 99.0 | 6.0 |
| γ | | — | — | 0.1 | 0.05 | 0.025 |
| | | | | 78.0 | 15.0 | 10.0 |
| Ω | | — | — | 0.1 | — | — |
| | | | | 30.0 | | |
| | With subcutaneous injection | | | | |
| Whole Mash (lyophilized) | Dose (mg/kg) | 200.0 | 100.0 | 50.0 | 25.0 |
| | Efficacy % | 100.0 | 100.0 | 100.0 | 70.0 |
| α | Dose (mg/kg) | 1.0 | 0.2 | 0.1 | |
| | Efficacy % | 100.0 | 99.5 | 60.0 | |

EXAMPLE 9
The anthelmintic activity of LL-F28249α against parasitic nematodes in sheep This experiment is designed to evaluate the activity of LL-F28249α against the economically important parasites of sheep. The sheep are experimentally inoculated with infective larvae of *Haemonchus contortus, Otertagia circumcincta* and *Trichostrongylus coluriformis*, to build up infections against which LL-F28249α will be challenged. Twenty-one days after inoculation, infection levels are determined by standard stoll count nematode counting procedures to determine the number of eggs of each species per gram of feces. The sheep are assigned randomly across three replicates of treatment and control groups based upon nematode egg counts. Twenty-two days after infection the sheep are treated with LL-F28249α using the doses and routes of administration shown in Table X below. Seven and eight days after treatment, the sheep are sacrificed and the worms are recovered using standard anthelmintic evaluation procedures. The efficacy of each treatment against each species is determined by comparing the number of worms at the respective dosage rate against the number of worms recovered in the three untreated control animals. The results of these evaluations, summarized in Table X below, demonstrates the high degree of effectiveness of LL-F28249α as an anthelmintic agent.

TABLE X

Anthelmintic efficacy of F28249α against Haemonchus, Ostertagia and Trichostrongylus in sheep

| Dose mg/kg | Route of administration | Efficacy (%) against | | |
|---|---|---|---|---|
| | | Haemonchus | Ostertagia | T. colubriformis |
| 1.0 | oral | 100.0 | 100.0 | 99.9 |
| 0.2 | oral | 100.0 | 100.0 | 99.9 |
| 0.1 | oral | 100.0 | 95.4 | 99.9 |
| 1.0 | IM | 100.0 | 100.0 | 100.0 |
| 0.2 | IM | 100.0 | 100.0 | 100.0 |
| | | Mean number of worms recovered (range) | | |
| 0.0 | — | 2683.0 | 881.0 | 16200.0 |

IM = Intermuscular

EXAMPLE 10

Efficacy of antibiotic LL-F28249α against the parasitic insect, *Melophagus ovinus*, (the sheep ked) on sheep This experiment is conducted concurrently on the same sheep used for the determination of anthelmintic activity as reported in Example 9. During the handling of the sheep prior to treatment, said sheep are observed for harbouring of natural infestations of *M. ovinus*. One half of each sheep is inspected for the indications of anti-ectoparasitic activity at necropsy, seven days after treatment.

The left side of each sheep is slowly sheared with electric clippers and inspected for living and dead sheep keds. The degree of infestation is approximated by the numbers of pupae found in the wool during the inspection and are rated 0 through +++, indicating no pupae to many pupae. The number of keds are recorded for each sheep, without knowledge of the treatment levels to eliminate bias. Initially, the keds were scored as alive or dead, but as experience was gained, some keds were scored as moribund because of abnormally-slow behavior.

Although there is a wide variation in the number of keds found on the sheep, the data summarized in Table XI below demonstrate that LL-F28249α is effective against *M. ovinus* and that said agent possesses systemic ecto-parasiticide activity. In treated animals the number of live keds is effectively reduced and the number of dead keds increased in the intramuscularly-treated sheep.

TABLE XI

Efficacy of agent F28249α against *Melophagus ovinus* on sheep

| Dose mg/kg | Route of administration | Mean number of keds[a] | | % |
|---|---|---|---|---|
| | | Alive | Dead | |
| 1.0 | Intramuscular | 1.67 | 1.67 | 78.22 |
| 0.2 | Intramuscular | 1.0 | 4.33 | 86.96 |
| 1.0 | Oral | 7.67 | 0.0 | 0.0 |
| 0.2 | Oral | 2.67 | 3.0 | 65.0 |
| 0.1 | Oral | 22.0 | 1.67 | 0.0 |
| Control | None | 7.67 | .67 | — |

[a]Three sheep per dose

[b]Efficacy % = 100 × (Mean number in control − mean number in treated) / Mean number in control

What is claimed is:

1. A method for the prevention, treatment or control of helmintic, arthropod ectoparasitic or acaridal infections in warm-blooded animals, said method comprising: orally, parenterally or topically administering to an animal infected with helminths, arthropod ectoparasites or acarides, a prophylactically, therapeutically or pharmaceutically-effective amount of the fermentation broth or whole mash of microorganism Streptomypes sp. LL-F28249, having deposit accession number NRRL 15773.

2. A method for the control of plant nematodes, said method comprising: applying to the foliage of plants, the soil in which they are grown, or into the trunks thereof, a nematocidally-effective amount of the fermentation broth or whole mash of microorganism Streptomyces sp. LL-F28249, having deposit accession number NRRL 15773.

3. An animal feed composition for the prevention, treatment or control of helmintic, arthropod ectoparasitic or acaridal infections in meat-producing animals, said animal feed composition comprising: an edible solid carrier; and a phophylactically, therapeutically or pharmaceutically-effective amount of the fermentation broth or whole mash of microorganism Streptomyces sp. LL-F28249, having deposit accession number NRRL 15773.

4. A composition according to claim 3, wherein said effective amount is about 0.00001% to 5%, by weight, of said composition.

* * * * *